(12) United States Patent
Raghavan et al.

(10) Patent No.: US 9,969,696 B2
(45) Date of Patent: May 15, 2018

(54) COMPOUNDS AS INHIBITOR OF DNA DOUBLE-STRAND BREAK REPAIR, METHODS AND APPLICATIONS THEREOF

(71) Applicant: INDIAN INSTITUTE OF SCIENCE, Bangalore, Karnataka (IN)

(72) Inventors: Sathees Chukkurumbal Raghavan, Bangalore (IN); Mrinal Srivastava, Bangalore (IN); Subhas Somalingappa Karki, Bangalore (IN); Bibha Choudhary, Bangalore (IN)

(73) Assignee: INDIAN INSTITUTE OF SCIENCE, Karnataka (IN)

( * ) Notice: Subject to any disclaimer, the term of this patent is extended or adjusted under 35 U.S.C. 154(b) by 0 days. days.

(21) Appl. No.: 14/412,912

(22) PCT Filed: Mar. 7, 2013

(86) PCT No.: PCT/IB2013/051798
§ 371 (c)(1),
(2) Date: Jan. 5, 2015

(87) PCT Pub. No.: WO2014/006518
PCT Pub. Date: Jan. 9, 2014

(65) Prior Publication Data
US 2015/0158822 A1    Jun. 11, 2015

(30) Foreign Application Priority Data
Jul. 4, 2012 (IN) .......................... 2713/CHE/2012

(51) Int. Cl.
C07D 239/48 (2006.01)
A61K 31/505 (2006.01)
C07D 487/14 (2006.01)
C07D 239/49 (2006.01)
C07D 475/12 (2006.01)
C12N 9/99 (2006.01)

(52) U.S. Cl.
CPC .......... *C07D 239/48* (2013.01); *A61K 31/505* (2013.01); *C07D 239/49* (2013.01); *C07D 475/12* (2013.01); *C07D 487/14* (2013.01); *C12N 9/99* (2013.01)

(58) Field of Classification Search
CPC ... C07D 239/48; C07D 239/49; A61K 31/505
USPC .......................................... 544/311; 514/274
See application file for complete search history.

(56) References Cited

U.S. PATENT DOCUMENTS

2009/0318456 A1   12/2009   Herdewijn et al.
2010/0099683 A1   4/2010    Tomkinson et al.

OTHER PUBLICATIONS

Youzhi Li et al., Suppressino of cancer relapse and metastasis by inhibiting cancer stemness, PNAS, vol. 112, No. 6, pp. 1839-1844 (2015).*
Johnson et al., Relationships between drug activity in NCI preclinical in vitro and in vivo models and early clinical trials, British Journal of Cancer, 84(10):1424-1431,2001.*
Pearce et al., Failure modes in anticancer drug discovery and development, Cancer Drug Design and Discovery Edited by Stephen Neidle, Chapter 18, pp. 424-435 (2008).*
Simone, Oncology: Introduction, Cecil Textbook of Medicine, 20th Edition, vol. 1, pp. 1004-101 O, 1995.*
Gura et al., Systems for identifying new drugs are often faulty, Science, 278:1041-1042, 1997.*
El Safty et al., Efficient adsorbents of nanoporous aluminosilicate monoliths for organic dyes from aqueous solution, Journal of Colloid and Interface Science, 359, pp. 9-18, (Jul. 1, 2011).*
Yoneda et al., Unequivocal Synthesis of 6-Arylpteridines by Intramolecular Cycloaddition of Azahexatrienes, Journal of the Chemical Society, Perkin Transactions 1, Issue 11, pp. 1336-1339, 1977.*
Schneider et al., Pteridines, LXI: Synthesis and Properties of Thiolumazines, Chem. Ber. 107, pp. 3377-3394 (1974).*
Abunada et al., Nitrilimines in 1,3-Dipolar Cycloaddition Reactions: Synthesis of New Derivatives of Condensed 1,2,4-Triazolo-Heterocycles and Dithiatriazaspiro[4,4]non-2-enone Derivatives, Jordan Journal of Chemistry, vol. 3, No. 1, pp. 1-10 (2008).*
Abdallah et al., A Novel Synthesis of 1,2,4-Triazolopteridines, Molecules, pp. 494-500 (2002).*
Ochoa et al., Anthelminitic Activity of 6,7-diaryl-pteridines, Arzneim. -Forsch./Drug Res. 46(I), pp. 643-648 (1996).*
Jarrahpour et al., "Synthesis, Antibacterial, Antifungal, and Antiviral Activity Evaluation of Some New bis-Schiff Bases of Isatin and their Derivatives," Molecules, Aug. 2007, vol. 12, pp. 1720-1730.
Srivastava et al., "An Inhibitor of Nonhomologous End-Joining Abrogates Double-Strand Break Repair and Impedes Cancer Progression," Cell, Dec. 2012, vol. 151, pp. 1474-1487.
Mondal et al., "Synthesis of Novel Mercapto-Pyrimidine and Amino-Pyrimidine Derivatives of Indoline-2-One as Potential Antioxidant & Antibacterial Agents," The Pharma Research, Jun. 2010, vol. 3, pp. 17-26.
Chen et al., "Rational Design of Human DNA Ligase Inhibitors that Target Cellular DNA Replication and Repair," Cancer Research, May 2008, vol. 68, pp. 3169-3177.
Sep. 20, 2014 International Search Report issued in International Application No. PCT/IB2013/051798.

* cited by examiner

*Primary Examiner* — Deepak R Rao
(74) *Attorney, Agent, or Firm* — Oliff PLC

(57) ABSTRACT

The present disclosure relates to compound of structural "formula I" and a method for preparing a compound of structural formula I. The disclosure further relates to a method of arresting DNA double-strand break (DSB) repair by employing the compound of structural formula I.

20 Claims, 40 Drawing Sheets

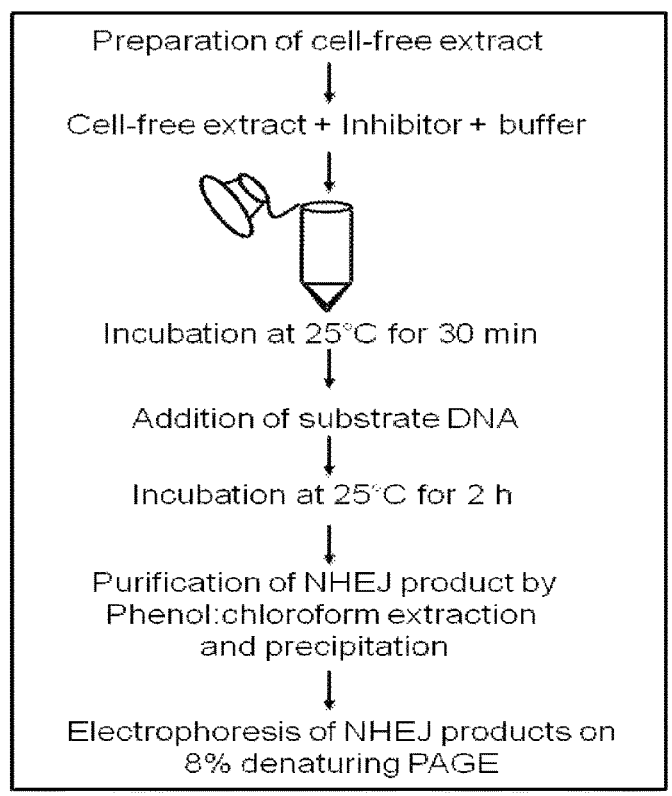
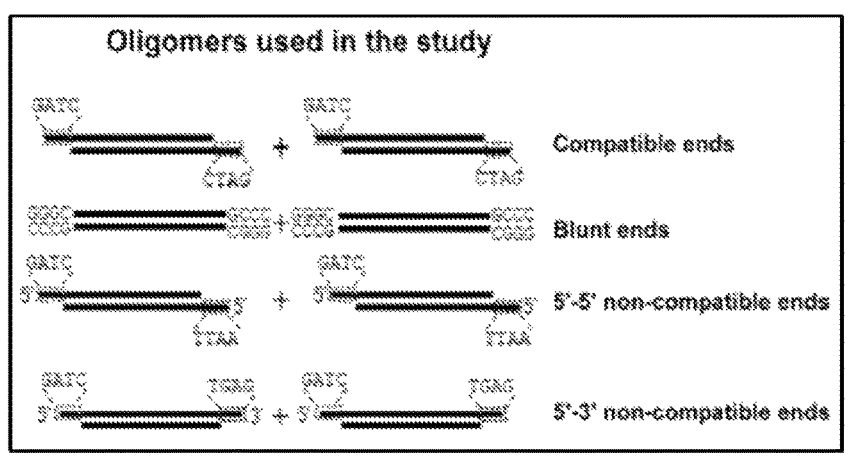
Figure 2A

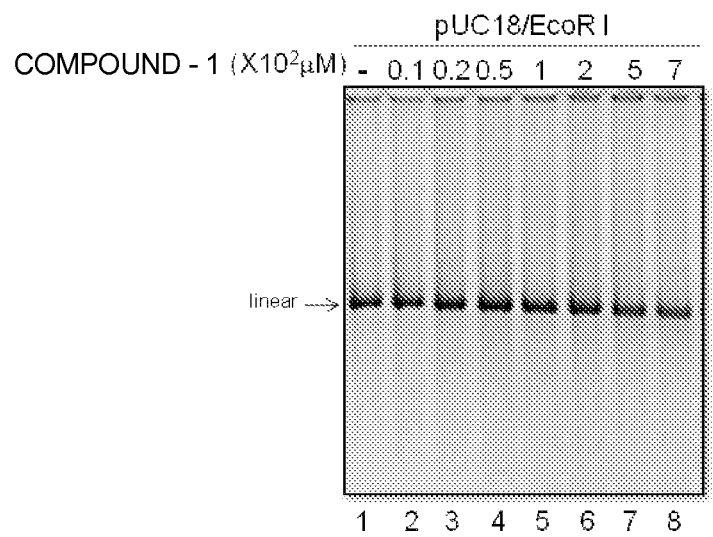
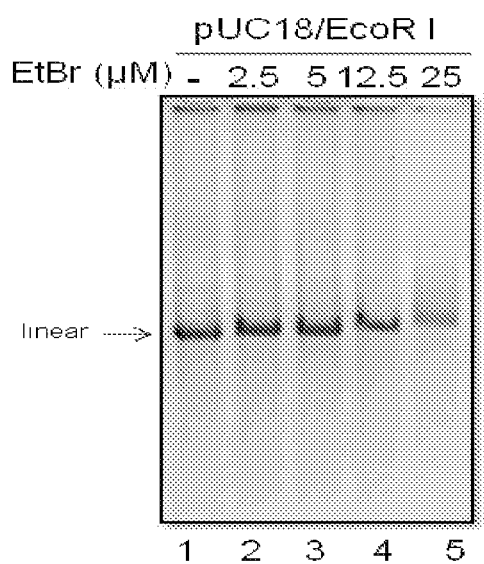
Figure 2D

| Oligomer | Sequence |
|---|---|
| TSK1 | 5'-ATCCCTCTAGATATCGGGCCCTCGATCCGGTACTACTCGAGCCGGCTAGCTTCGATGCTGCAGTCTAGCCTGAG-3' |
| TSK2 | 5'-ATCCTCAGGCTAGACTGCAGCATCGAAGCTAGCCGGCTCGAGTAGTACCGGATCGAGGGCCCGATATCTAGA-GG-3' |
| VK7 | 5'-GGGCTCTAGATATCGGGCCCTCGATCCGGTACTACTCGAGCCGGCTAGCTTCGATGCTGCAGTCTAGCCTGGC-CC-3' |
| VK8 | 5'-GGGCCAGGCTAGACTGCAGCATCGAAGCTAGCCGGCTCGAGTAGTACCGGATCGAGGGCCCGATATCTAGAGCCC-3' |
| VK11 | 5'-AATTCTCAGGCTAGACTGCAGCATCGAAGCTAGCCGGCTCGAGTAGTACCGGATCGAGGGCCCGATATCTAGAGG-3' |
| VK13 | 5'-GGCTAGACTGCAGCATCGAAGCTAGCCGGCTCGAGTAGTACCGGATCGAGGGCCCGATATCTAGAGG-3' |
| MS42 | 5'-TGGATCCATGGCTGCCTCACAAAC-3' |
| MS43 | 5'-CCTCGAGCTCACTAGGAAACCTAGC-3' |
| MS48 | 5'-ATTCGGATCCATGGTGCGGTCGG-3' |
| MS49 | 5'-CTATGCGGCCGCCTATATCATGTCC-3' |
| MS52 | 5'-GAATTCATGTCAGGGTGGGAGTC-3' |
| MS53 | 5'-CATATGATATCTCCTTCTTATCAGTCCTGG-3' |
| MS61 | 5'-TTACTCGAGAGCTAGCATTGG -3' |
| MS68 | 5'-ATCCGTTGAAGCCTGCTT-3' |
| MS69 | 5'-TGACATACTAACTTGAGCGAAACGG-3' |
| MS70 | 5'-CCGTTTCGCTCAAGTTAGTATGTCAAAGCAGGCTTCAACGGAT-3' |

Figure 3

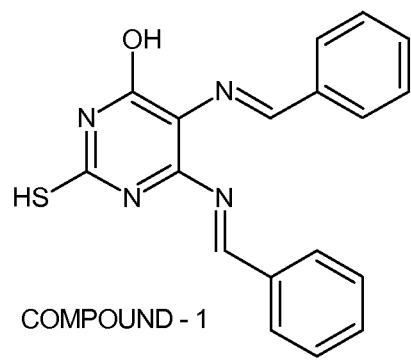
Figure 4(I) A
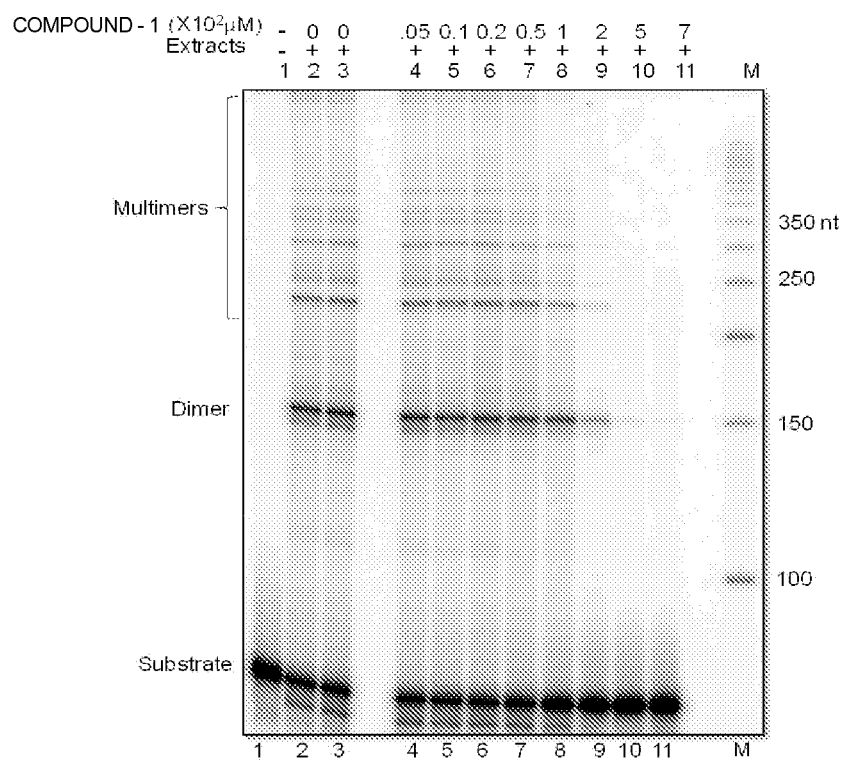
Figure 4(I) B

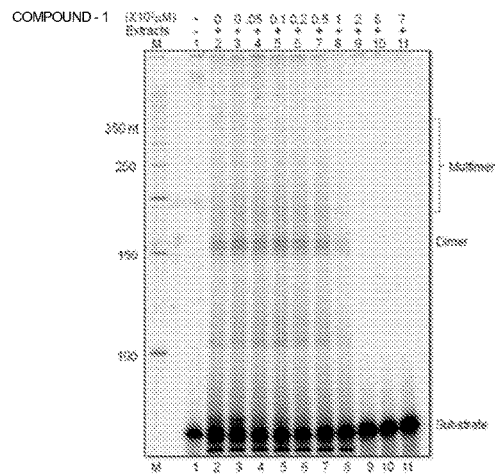
Figure 4(I) C
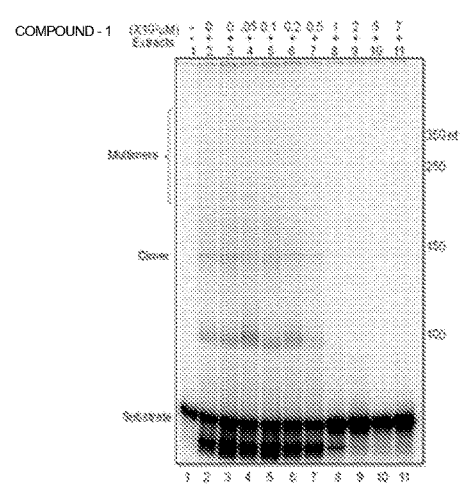
Figure 4(I) D
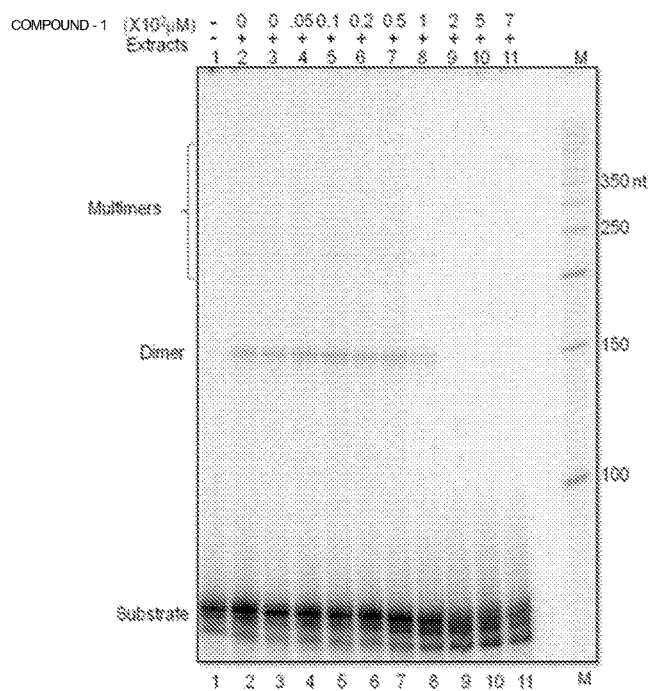
Figure 4(I) E

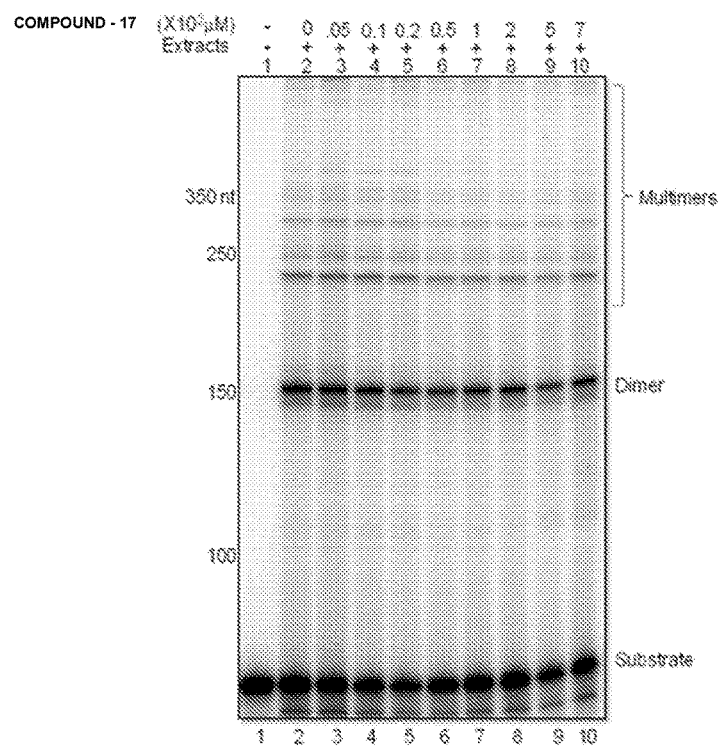
Figure 4(I) F
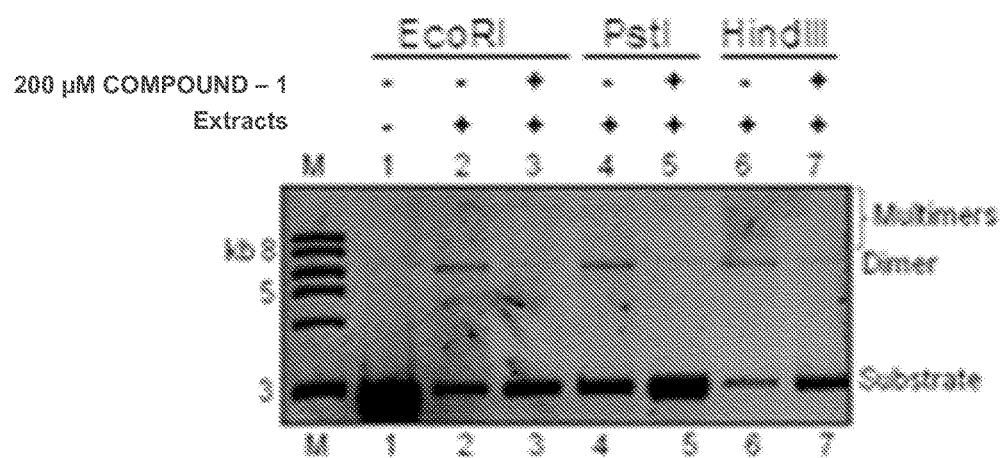
Figure 4(I) G

Compound - 21
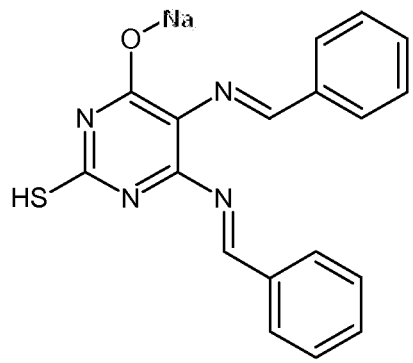
Figure 4(II) A
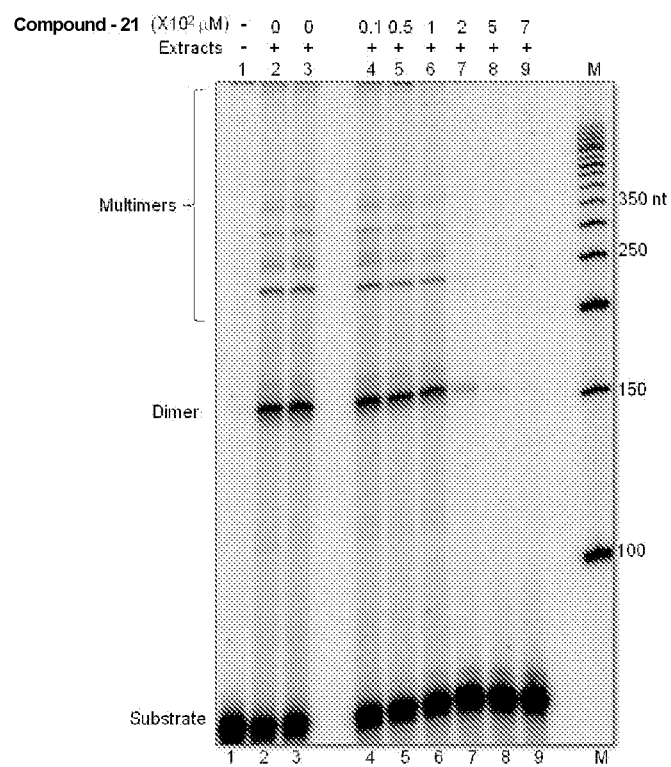
Figure 4(II) B

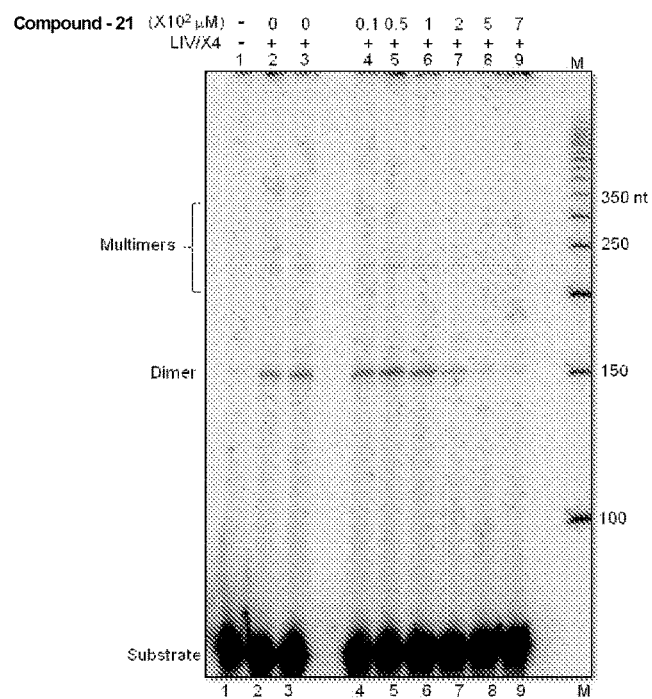
Figure 4(II) C
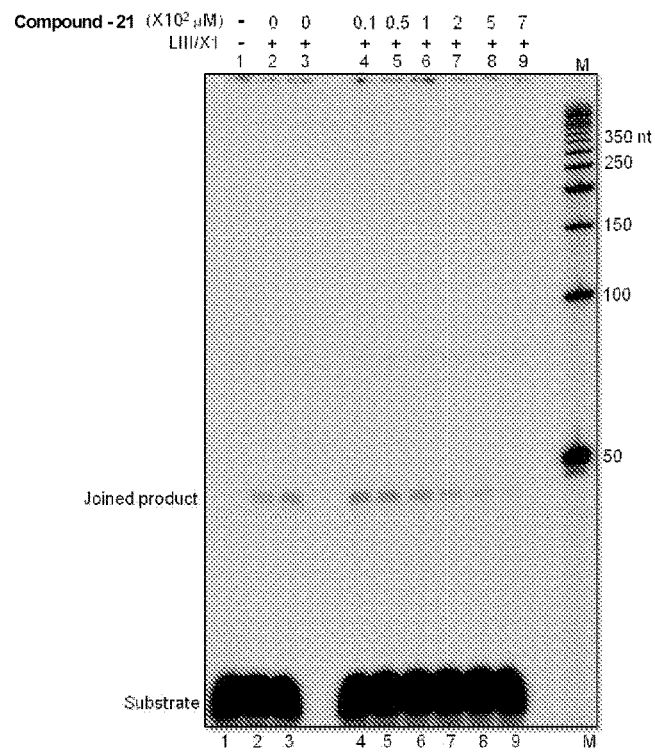
Figure 4(II) D

A

| Compound 1 (μM) | No. of Metaphases | Chromosomal Abnormality, Frequency |
|---|---|---|
| 20 | 25 | ND |
| 40 | 25 | ND |
| 100 | 22 | Chromosomal arm Breakage (7/22) |

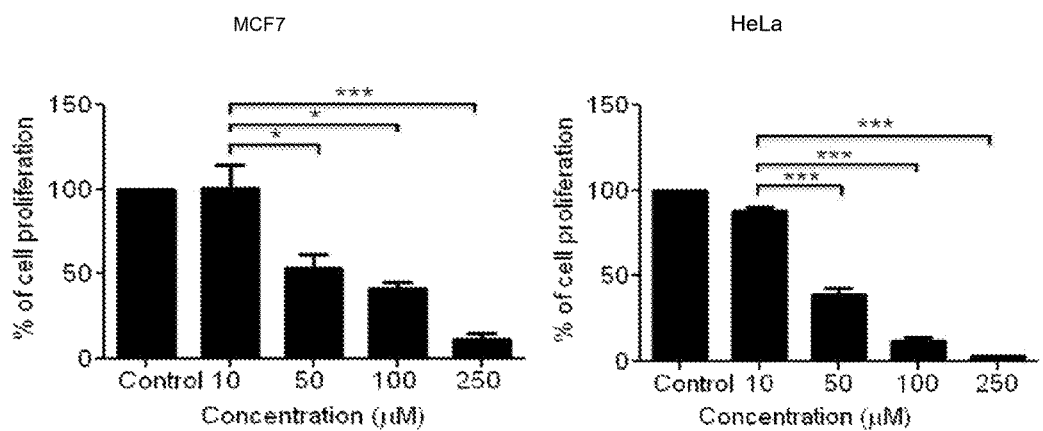
Figure 10 F
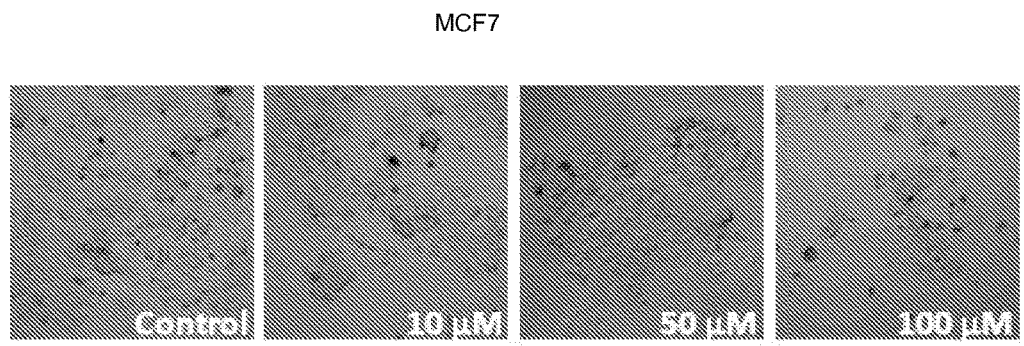
Figure 10 G
| Name | Cancer type | $IC_{50}$ (µM) |
|---|---|---|
| HeLa | Cervical | 40 |
| MCF7 | Breast | 40 |
| A549 | Lung | 35 |
| HT1080 | Fibrosarcoma | 60 |
| A2780 | Ovarian | 15 |
| K562 | Myeloid leukemia | >100 |
| CEM | Leukemia | >100 |
Figure 10 H

| Functional tests | 28th day | |
|---|---|---|
| | Control | Compound-1 Treated |
| Alkaline phosphatase (ALP) | 45.3±5.69 | 54.24±5.19 |
| Alanine aminotrasferase (ALT) | 42.08±14.26 | 43.98±6.71 |
| Creatinine | 0.38±0.1 | 0.33±0.06 |
| Urea | 36.38±4.43 | 41.18±3.48 |

COMPOUNDS AS INHIBITOR OF DNA DOUBLE-STRAND BREAK REPAIR, METHODS AND APPLICATIONS THEREOF

TECHNICAL FIELD

The present disclosure relates to compound of structural 'formula I' and method for preparing a compound of structural formula I. The disclosure further relates to a method of arresting DNA double-strand break (DSB) repair by employing the compound of structural formula I.

BACKGROUND AND PRIOR ART OF THE DISCLOSURE

The treatment of cancer has undergone evolutionary changes as understanding of the underlying biological processes has improved. Tumor removal surgeries have been documented in ancient Egypt, hormone therapy was developed in 1896, and radiation therapy in 1899. Chemotherapy, immunotherapy, and newer targeted therapies are products of the 20th century. As new information about the biology of cancer emerges, treatments are developed and modified to increase effectiveness, precision, survivability, and quality of life.

Radiotherapy and chemotherapy are commonly used treatments for various cancers and lead to the generation of double-strand breaks (DSBs) as intermediates during their action. Unresponsive and relapsed tumors are resistant to both these modalities. It is believed that NHEJ proteins which are involved in DNA double-strand break repair play a major role in providing resistance to cancer cells against these agents. Non-homologous end joining (NHEJ) is one of the two major pathways that repairs double-strand breaks in DNA. One of the enzymes involved in sealing of DSBs during NHEJ is DNA Ligase IV.

In a nutshell, there is a necessity to develop better and efficient therapies for managing cancer.

STATEMENT OF THE DISCLOSURE

Accordingly, the present disclosure relates to a compound of formula-I.

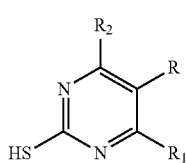

Formula I where, R is selected from a group comprising amine NR'R" and imine —N=C—R''', R$_1$ is selected from a group comprising amine NR'R" and imine —N=C—R''', R$_2$ is —OH, and R', R" and R''' are selected from a group comprising —H, alkyl and aryl or any combination thereof, and its tautomers, isomers, analogs, derivatives and salts thereof, wherein the compound comprises at least one imine group; a method for preparing a compound of formula-I,

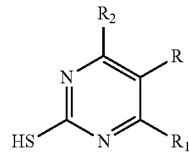

Formula I where, R is selected from a group comprising amine NR'R" and imine —N=C—R''', R$_1$ is selected from a group comprising amine NR'R" and imine —N=C—R''', R$_2$ is —OH, and R', R" and R''' are selected from a group comprising —H, alkyl and aryl or any combination thereof, and its tautomers, isomers, analogs, and derivatives thereof, wherein the compound comprises at least one imine group, comprising steps of:
a) reacting an amine substituted mercaptopyrimidine with a carbonyl compound to obtain a compound of formula I with imine functionality, and
b) optionally, reacting the compound of formula I of step (a), having an additional amine group, with a carbonyl compound by intermolecular or intramolecular fashion, to obtain the compound of formula I with diimine functionality; and a method of arresting DNA double-strand break (DSB) repair, said method comprising act of contacting a compound of formula-I with DNA Ligase for arresting the DNA double-strand break (DSB) repair.

BRIEF DESCRIPTION OF ACCOMPANYING FIGURES

In order that the disclosure may be readily understood and put into practical effect, reference will now be made to exemplary embodiments as illustrated with reference to the accompanying figures. The figures together with a detailed description below, are incorporated in and form part of the specification, and serve to further illustrate the embodiments and explain various principles and advantages, in accordance with the present disclosure where:

FIG. 1 depicts the characterization of Compound 1. FIGS. 1A and B depicts the characterization of Compound 1 by IR spectroscopy (A) and NMR spectrum of Compound 1 (B).

FIGS. 1C and D. depicts the LC MS/MS spectrum (C) with its chromatogram (D), indicating retention time and purity of the Compound 1.

FIG. 2 depicts the NHEJ assay and study of joining efficiency. A. Schematic representation of NHEJ assay and substrates containing DSBs.

FIG. 3 shows the list of oligomers used in the study.

FIG. 4(I) depicts the structural and functional characterization of putative Ligase IV inhibitor Compound 1 using DNA substrates possessing various DSBs. A. Chemical structure of Compound 1 [5,6-bis(benzylideneamino)-2-mercapto-pyrimidin-4-ol]. B. Effect of Compound 1 on joining of 5' compatible ends.

FIG. 4(I) C-E depicts the effect of Compound 1 on EJ of 5'-5' noncompatible (E), 5'-3' noncompatible (F) and blunt (G) ends.

FIG. 4(I) F depicts the effect of Ligase I inhibitor, Compound 17 on joining of 5' compatible ends catalysed by testicular extracts. G. Effect of Compound 1 on plasmid based EJ.

FIG. 4(II) depicts the structural and functional characterization of Compound 21. A. Chemical structure of Compound 21. B. Effect of Compound 21 on the joining of 5' compatible ends.

FIG. 4(II) C and D depicts the effect of Compound 21 on the joining catalyzed by purified Ligase IV/XRCC4 (C) and Ligase III/XRCC1 (D) on joining of 5' compatible ends and nicked substrates, respectively.

Figure 5:
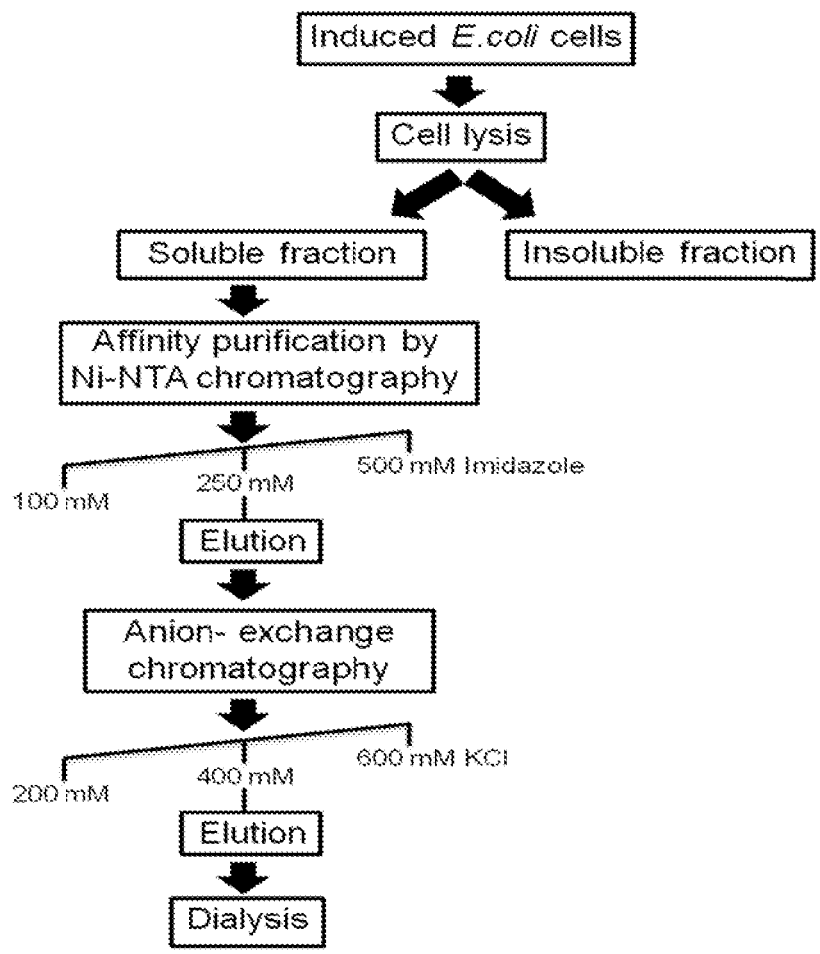
Figure 5:
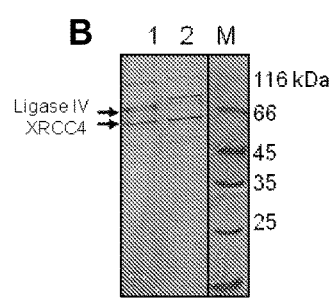
Figure 5:
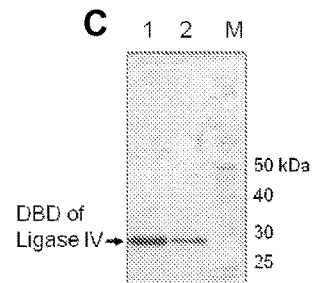
Figure 5:
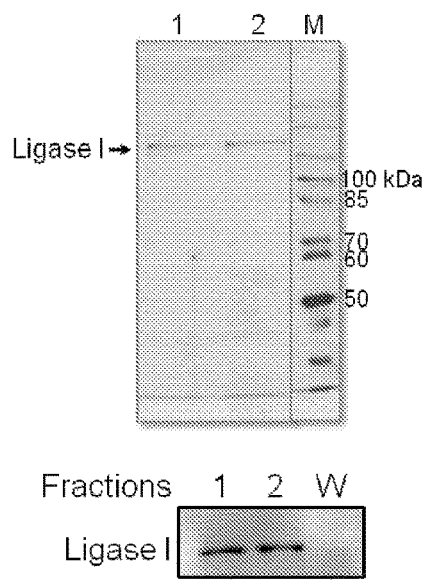
Figure 5:
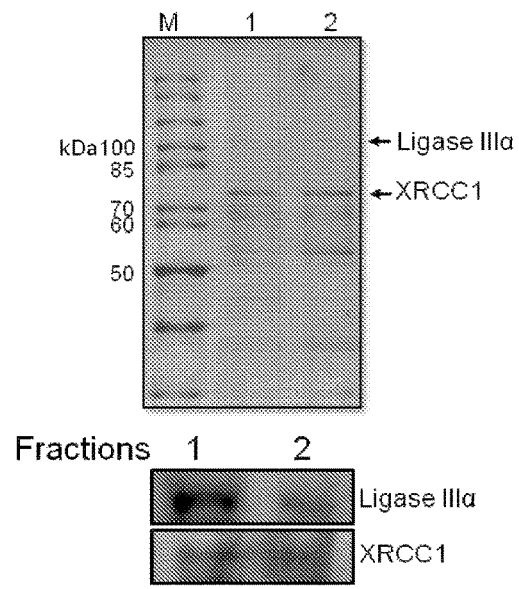

FIG. 5 depicts the overexpression and purification of Ligase IV/XRCC4, DBD Ligase IV, Ligase I and Ligase III. A. Schematic representation of strategy used for the purification of Ligase IV/XRCC4.

FIG. 5 B-E depicts the SDS-PAGE profile of eluted fractions of purified Ligase IV/XRCC4 (B), DBD of Ligase IV (C) Ligase I (D), Ligase IIIα/XRCC1 (E). Alternate fractions are loaded on the SDS-PAGE and visualized by silver staining.

Figure 6:
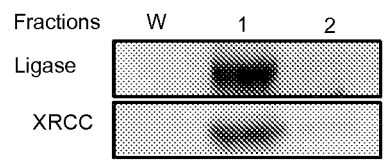
Figure 6:
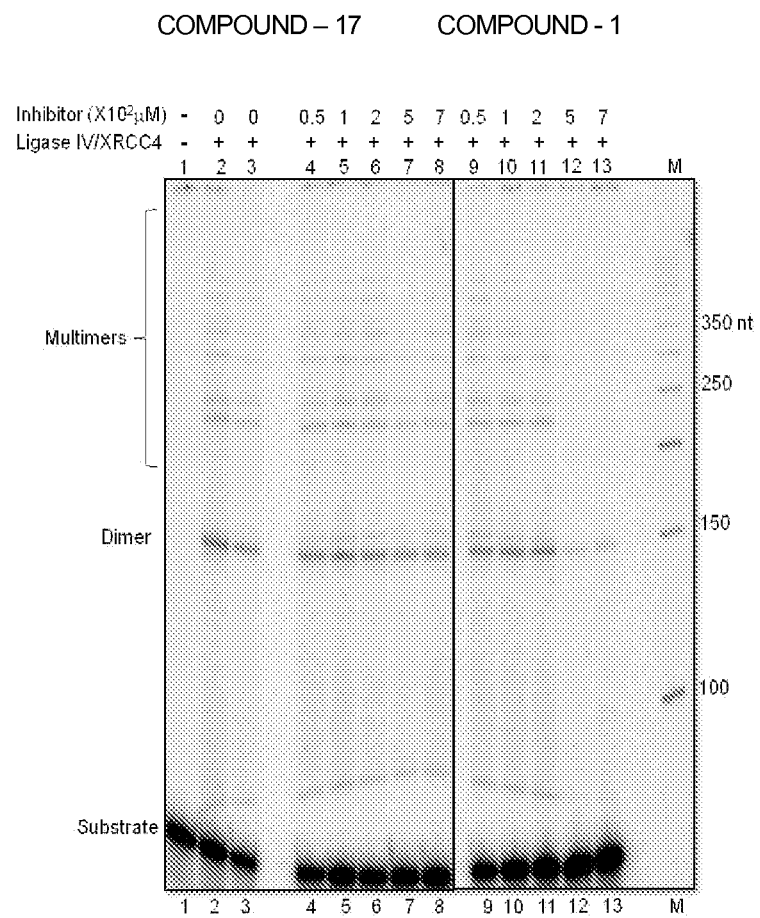
Figure 6:
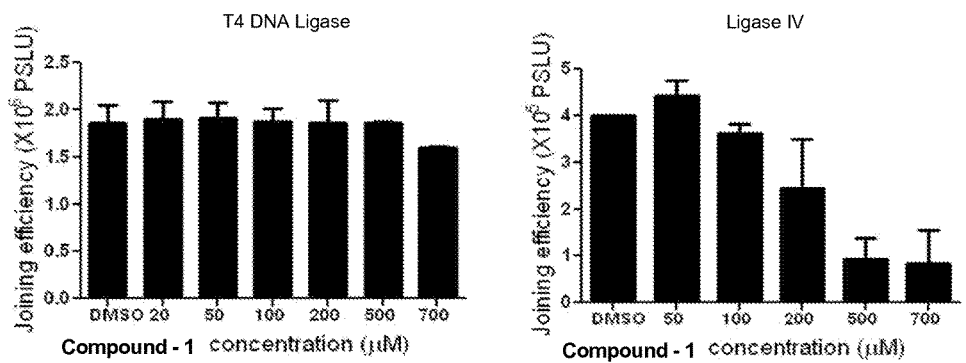
Figure 6:
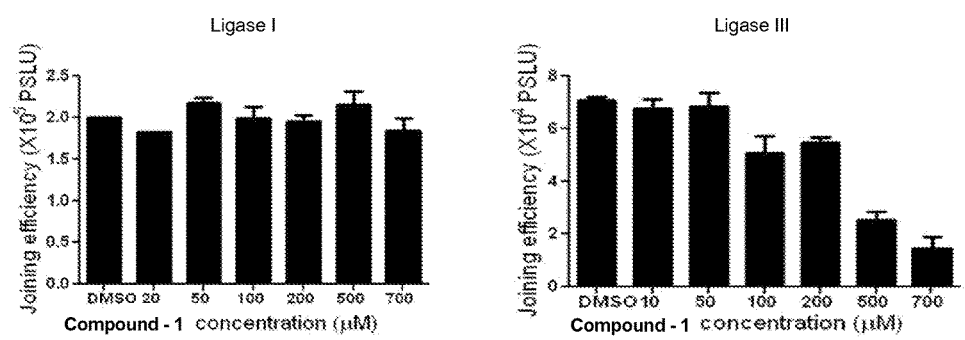
Figure 6:
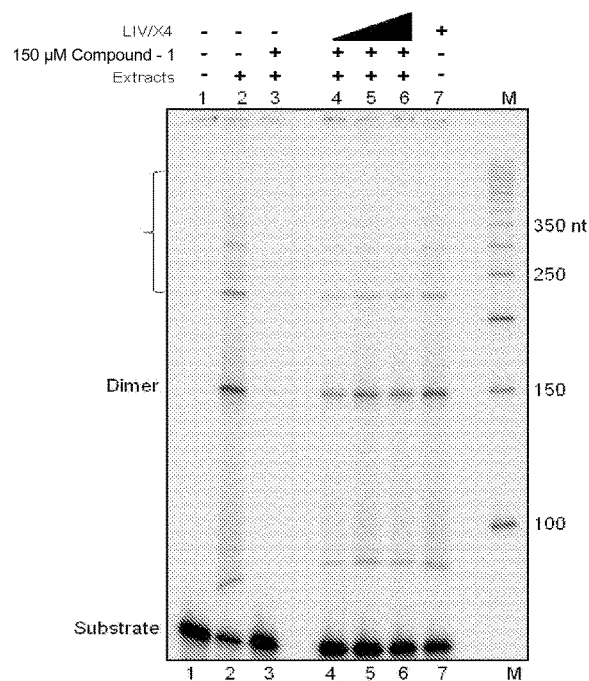
Figure 6:
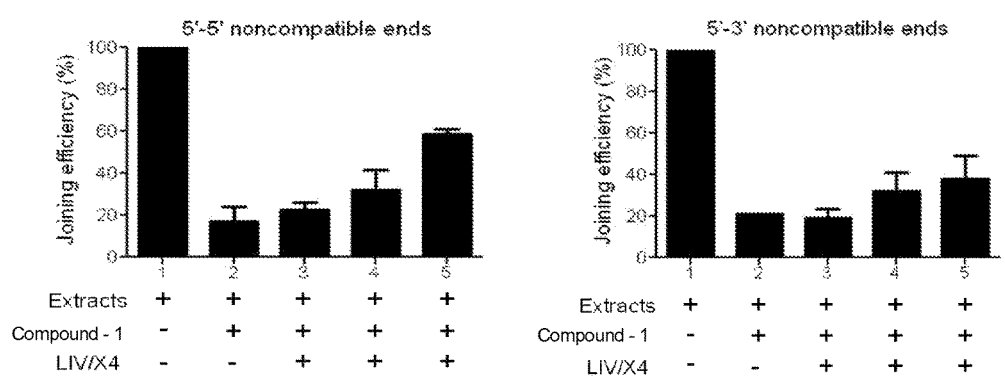

FIG. 6 depicts the effect of Compound 1 on DNA end joining catalysed by purified Ligase IV/XRCC4 complex and analysis of its specificity. A. Western blot showing presence of Ligase IV/XRCC4 in eluted fractions. B. Comparison of effect of Compound 17 and Compound 1 on DSB joining of 5' compatible ends catalysed by purified Ligase IV/XRCC4 complex (60 fmol).

FIGS. 6 C and D depict the bar diagram representing quantification of effect of Compound 1 on EJ of 5' complementary end catalysed by purified Ligase IV/XRCC4 complex (Right panel) or T4 DNA ligase (left panel) (C) and bar diagram representing quantification of effect of Compound 1 on ligation of a nick on a double-stranded oligomeric DNA substrate catalysed by purified Ligase I (left panel) or Ligase III (Right panel) (D).

FIGS. 6 E and F depicts the complementation of Compound 1 mediated inhibition of NHEJ by purified Ligase IV/XRCC4 complex (E) and bar diagram representing quantification of the complementation experiment performed on 5'-5' and 5'-3' noncomplementary ends (F) respectively.

Figure 7:
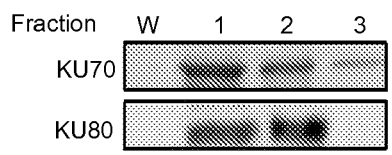
Figure 7:
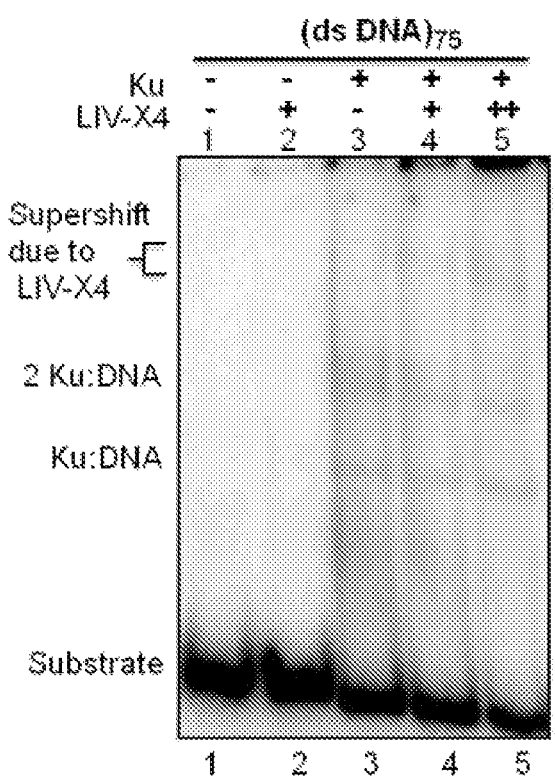
Figure 7:
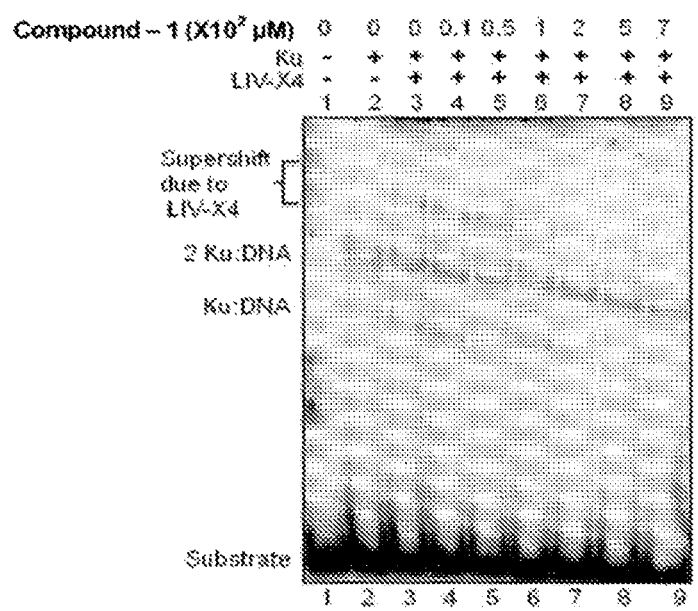
Figures 1, 7D:
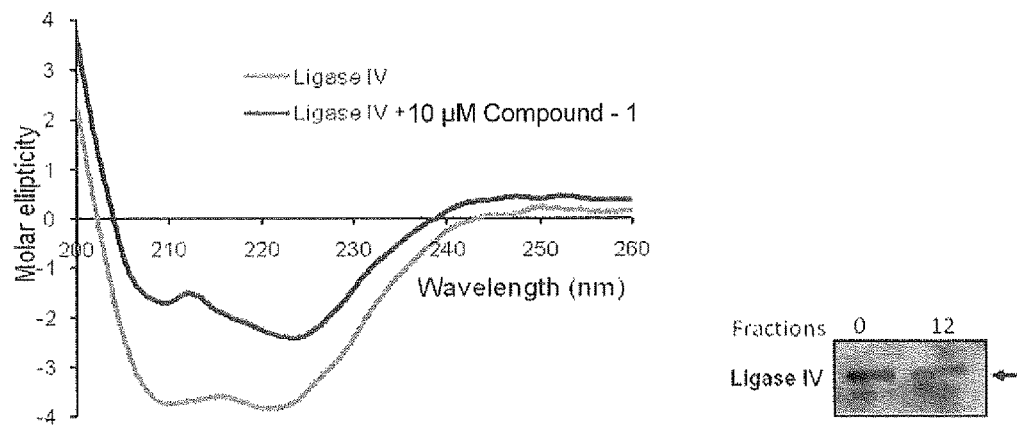
Figures 2, 7D:
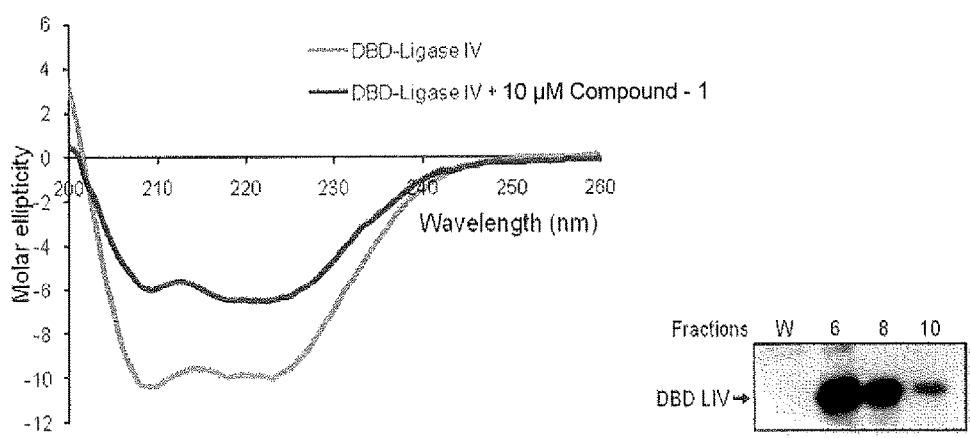

FIG. 7 depicts the evaluation of Compound 1 binding to the DNA binding domain of Ligase IV and its effect on binding to DSBs. A. Western blot analysis of KU70 and KU80 proteins in purified fractions. B. Binding of KU proteins to DNA breaks. C. Analysis of effect of Compound 1 on Ligase IV/XRCC4 complex binding to DNA. FIG. 7 D-1 and FIG. 7D-2 depict the CD spectroscopy to evaluate structural changes in Ligase IV and DBD upon binding to Compound 1.

Figure 8:
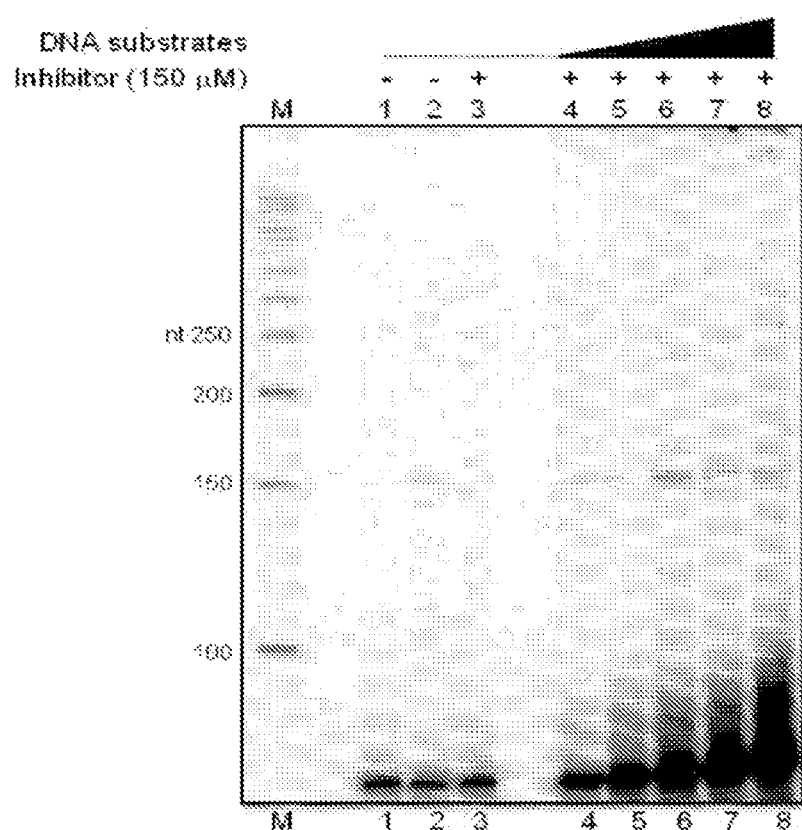
Figure 8:
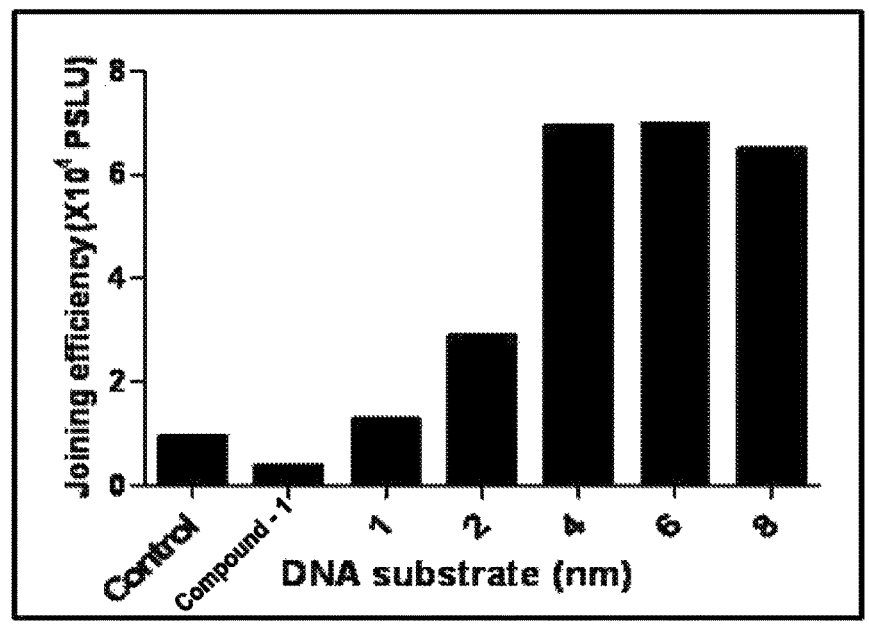

FIG. 8 depicts the effect of Compound 1 on joining efficiency of compatible ends when increasing concentrations of DNA substrates were used. A. Gel profile showing competition studies using increasing concentrations of DNA and Compound 1 for binding on Ligase IV. B. Image is analyzed and quantitated using Multi Gauge (ver 3.0) software and presented as a bar diagram.

Figure 9:
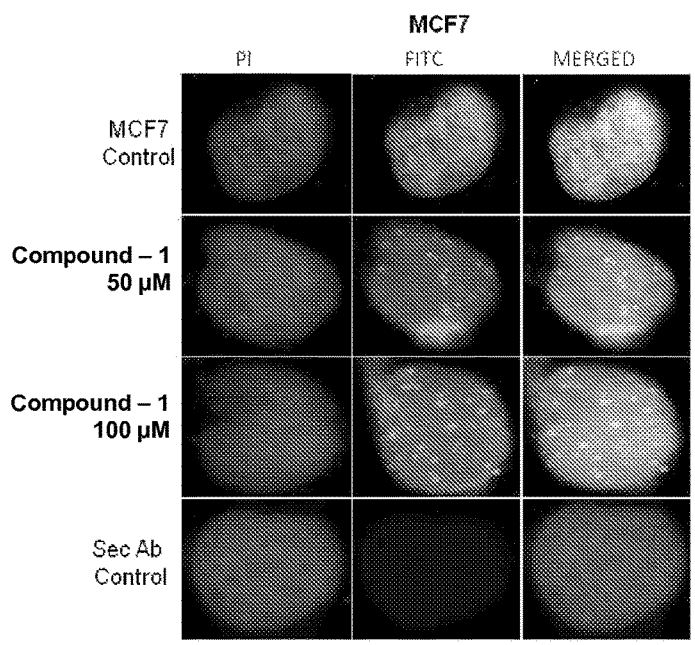
Figure 9:
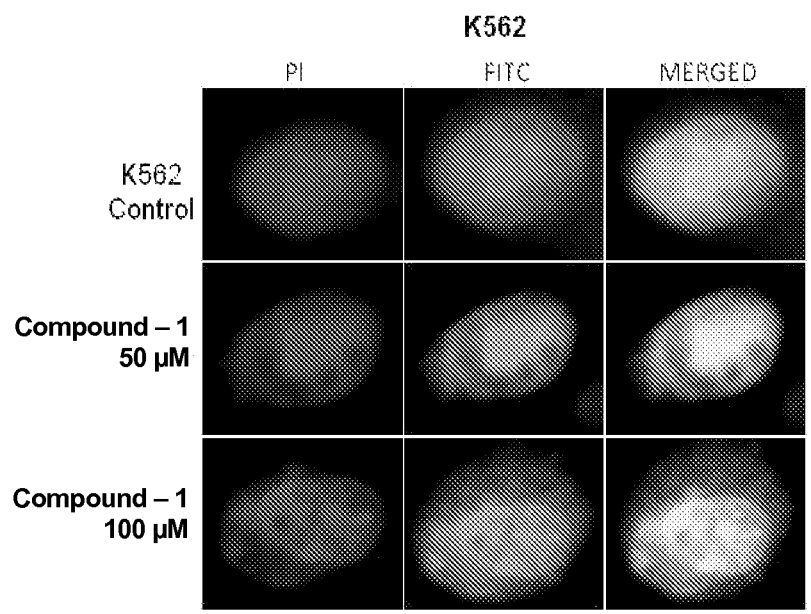
Figure 9:
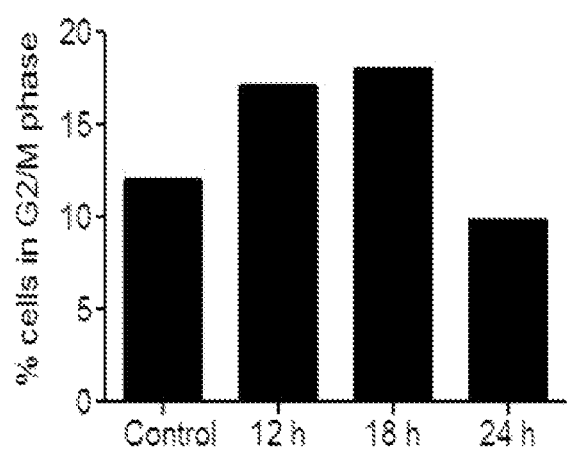
Figure 9:
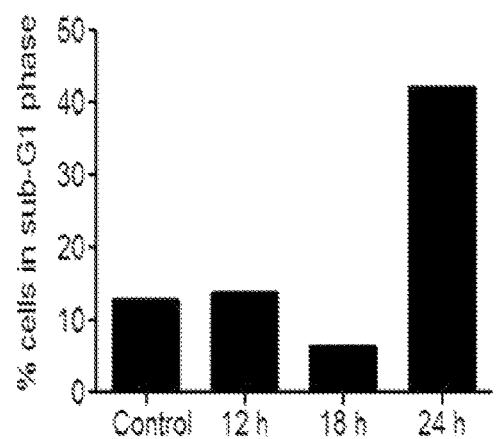
Figure 9:
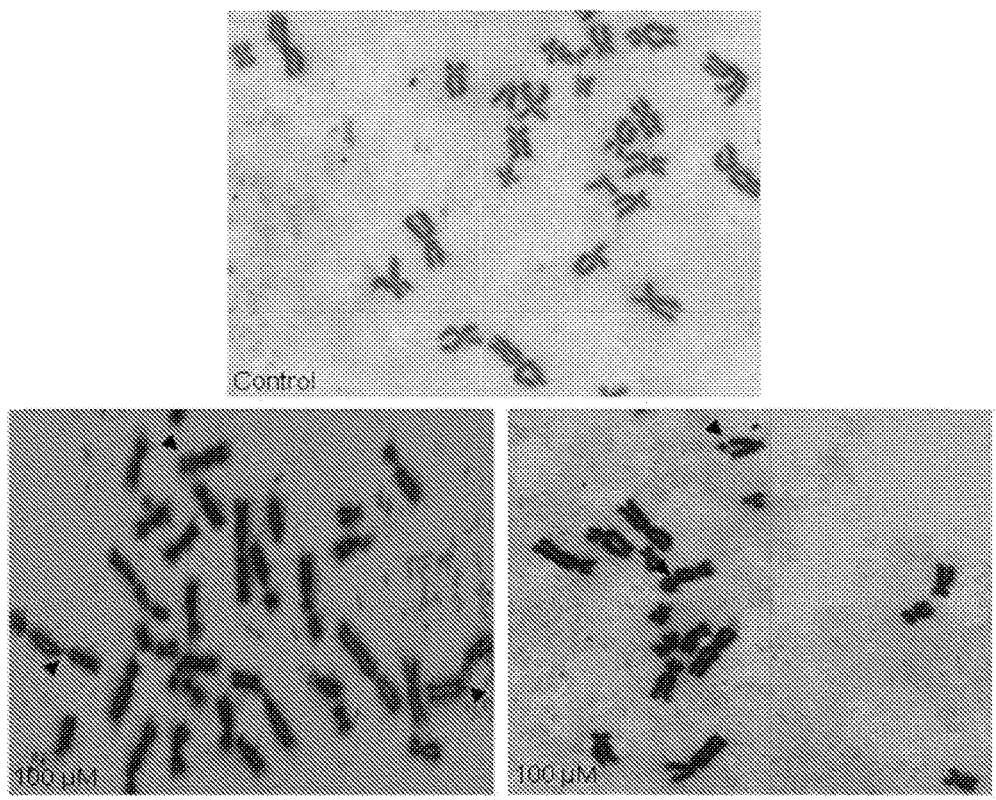

FIG. 9 depicts the effect of Compound 1 on chromosomal integrity and cell cycle progression. A. Immunofluorescence images of γH2AX foci formation in MCF7 cells following treatment with Compound 1 (50 and 100 μM). B. γH2AX foci formation in K562 cells following treatment with Compound 1 (50 and 100 μM).

FIGS. 9 C and D depicts the cell cycle analysis upon Compound 1 treatment.

FIG. 9 E depicts the effect of Compound 1 on induction of genomic instability and FIG. 9 F depicts the table showing summary of chromosomal breaks analyzed following Compound 1 treatment. "ND" is none detected.

Figures 9, 10:
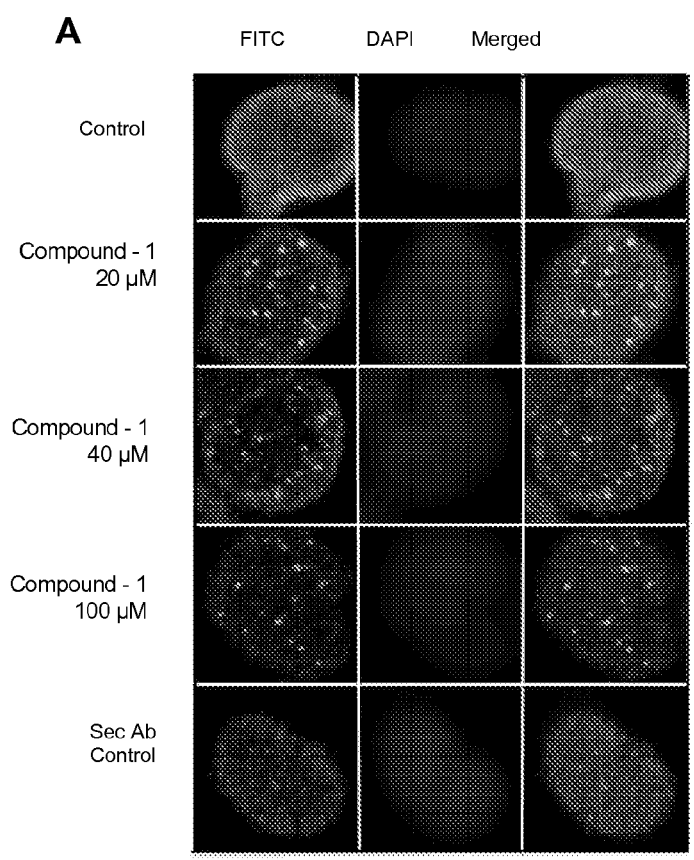
Figure 10:
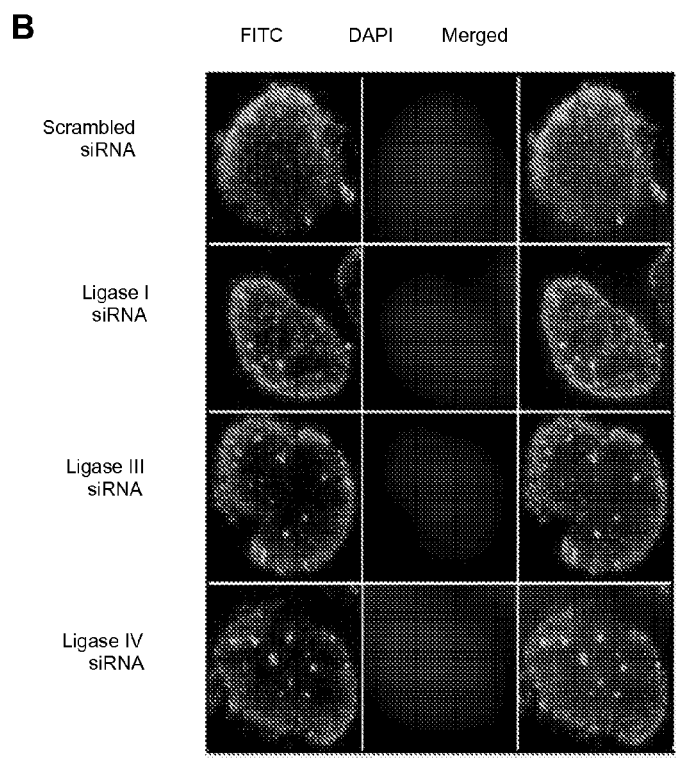
Figure 10:
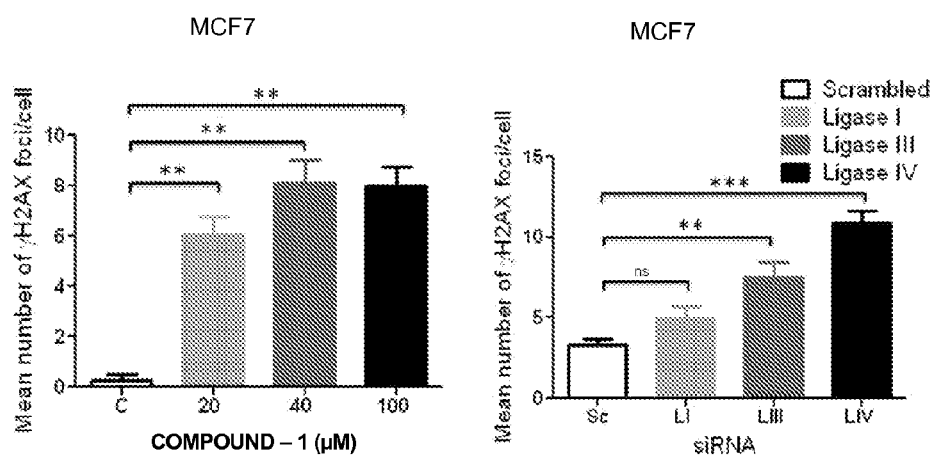
Figure 10:
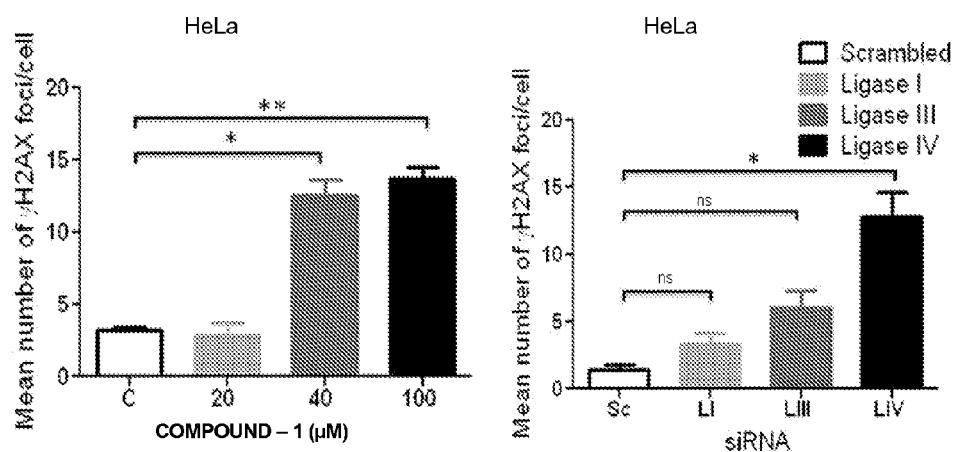
Figure 10:
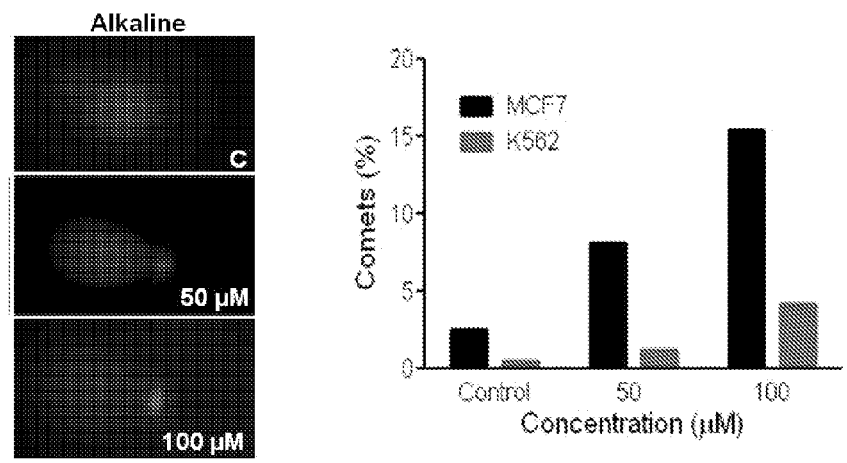

FIG. 10 depicts the evaluation of the effect of Compound 1 on NHEJ, accumulation of DSBs, and induction of cytotoxicity within the cells. A. Immunofluorescence showing γH2AX foci within MCF7 following treatment with Compound 1 (20, 40 and 100 μM, 24 h). B. Detection of DSBs by γH2AX foci formation in MCF7 cells following treatment with siRNA against Ligase I, Ligase III and Ligase IV.

FIG. 10 C, D depicts the bar diagram showing comparison of γH2AX foci in MCF7 (C) and HeLa (D) cells following treatment with different concentrations of Compound 1 and siRNA against different ligases.

FIG. 10 E depicts the PI stained images for MCF7 cells treated with Compound 1 (24 h) following alkaline single cell gel electrophoresis. FIG. 10 F depicts the comparison of cytotoxicity induced by Compound 1 on MCF7 and HeLa cells, as measured by MTT assay.

FIG. 10 G depicts the images of MCF7 cells treated with various concentrations of Compound 1 for about 5 days. FIG. 10 H depicts the comparison of $IC_{50}$ of Compound 1 based on MTT assay in different cancer cell lines.

Figure 11:
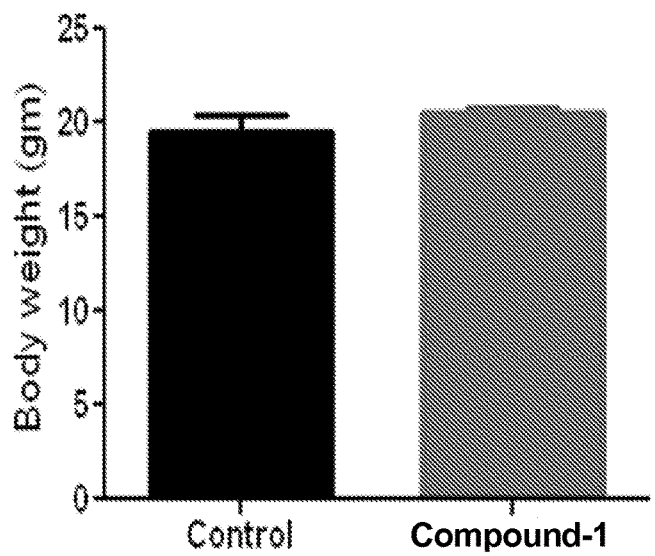

FIG. 11 depicts the assessment of side effects of Compound 1 treatment on mice. A. Bar graph represents average weight changes in both controls (n=10) and Compound 1 treated mice (n=7). B. Serum profile on mice administered with Compound 1 at day 28.

Figure 12:
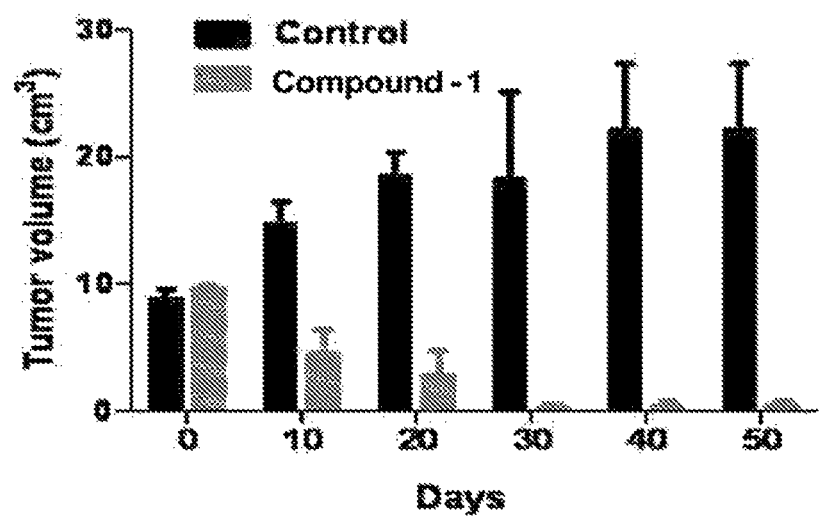
Figures 1, 12B:
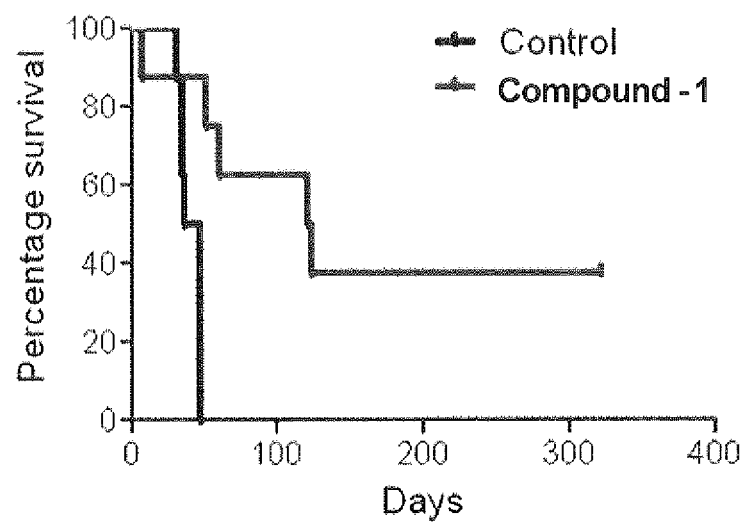
Figures 2, 12B:
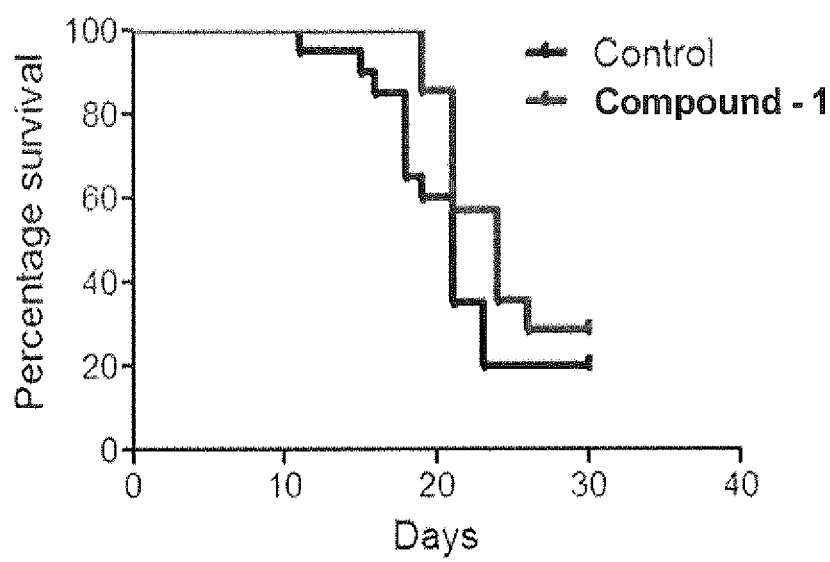
Figure 12:
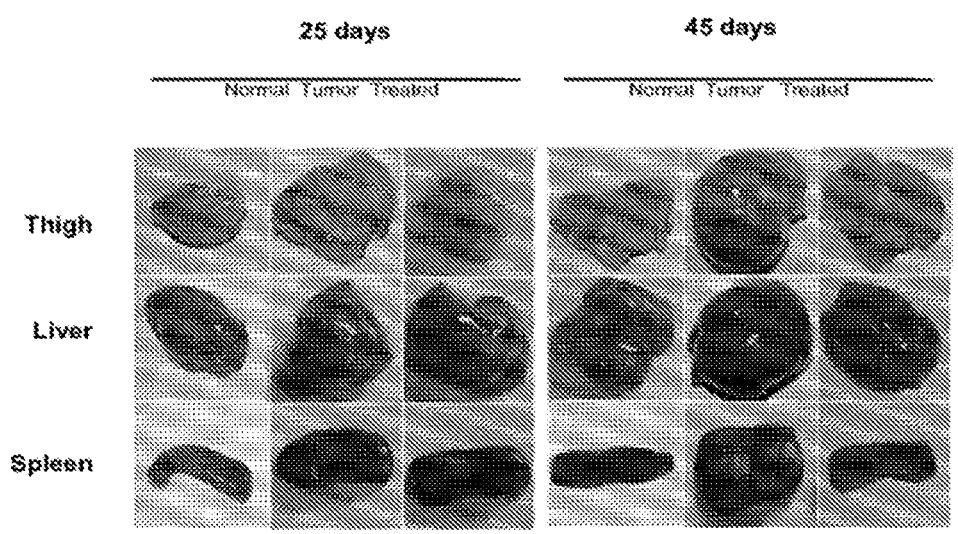
Figure 12:
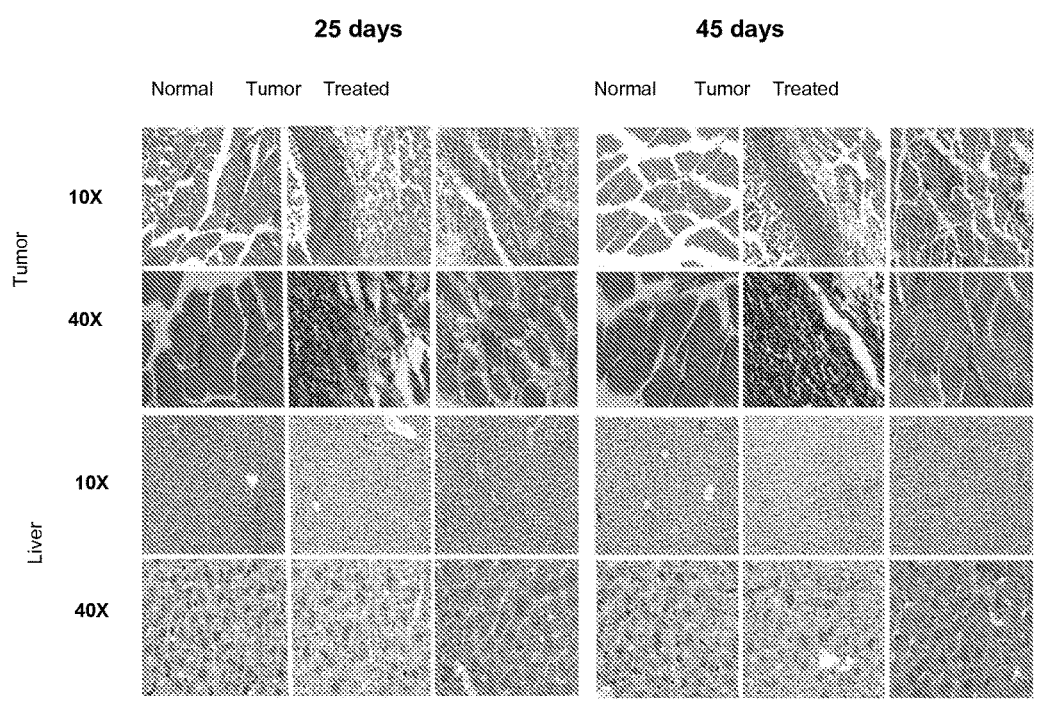

FIG. 12 depicts the effect of Compound 1 on tumor progression in mice models bearing various tumors. A. Comparison of solid tumor progression generated by breast adenocarcinoma cells following treatment with Compound 1. B-1 and B-2. Kaplan-Meier survival curves of Compound 1 treated Dalton's lymphoma mice for 30 days.

FIG. 12 C depicts the gross appearance of tumor and organs of mice following Compound 1 treatment after $25^{th}$ and $45^{th}$ days of tumor development and FIG. 12 D depicts the histopathology of the tumor and liver of mice following Compound 1 treatment after $25^{th}$ and $45^{th}$ days of tumor development.

Figure 13:
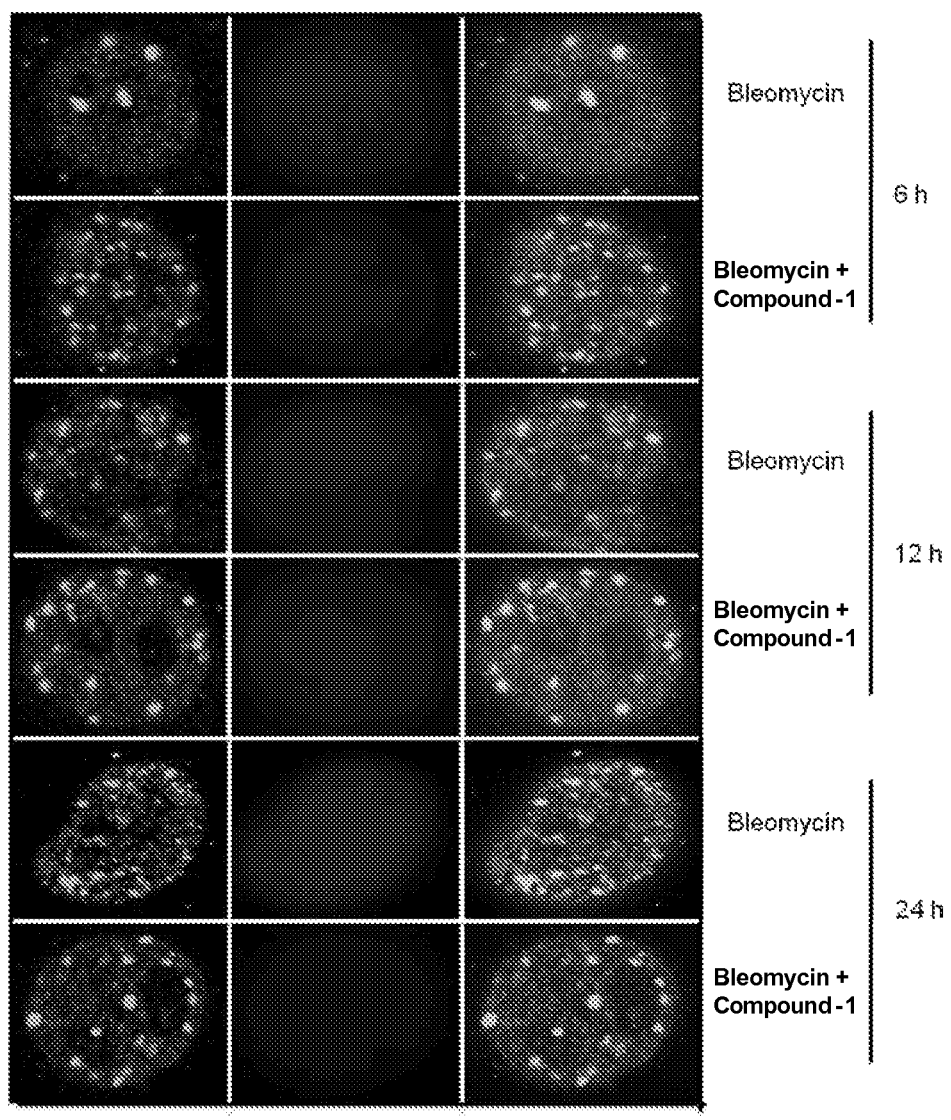
Figure 13:
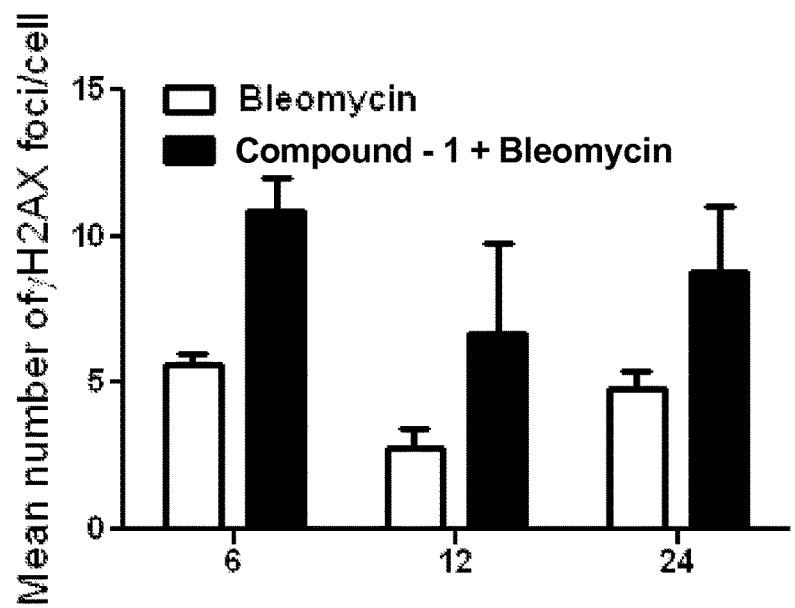

FIG. 13 depicts the effect of Compound 1 treatment on formation of DSBs with increase in time. A. HeLa cells are exposed to bleomycin for 3 h. Compound 1 (about 40 μM) is added to the cells following removal of bleomycin, and allowed to repair for the indicated time. Images are captured using Carl Zeiss laser confocal microscope.

FIG. 13 B depicts the bar diagram representing mean number of DSBs/cell.

Figure 14:
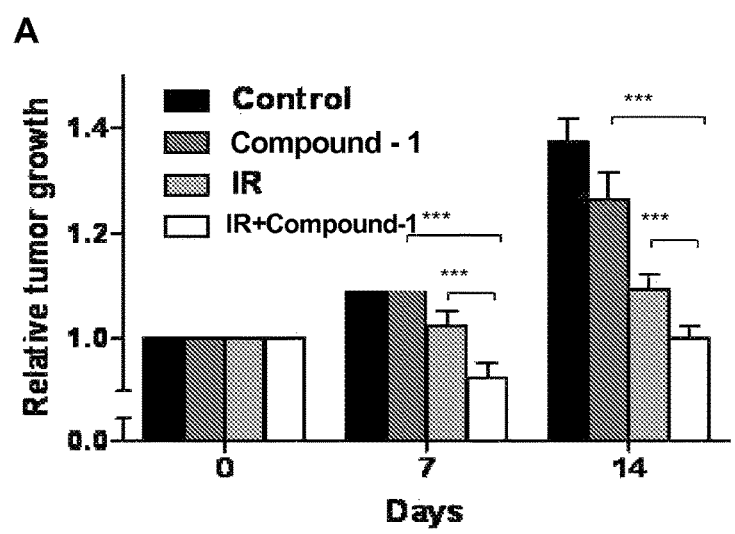
Figure 14B:
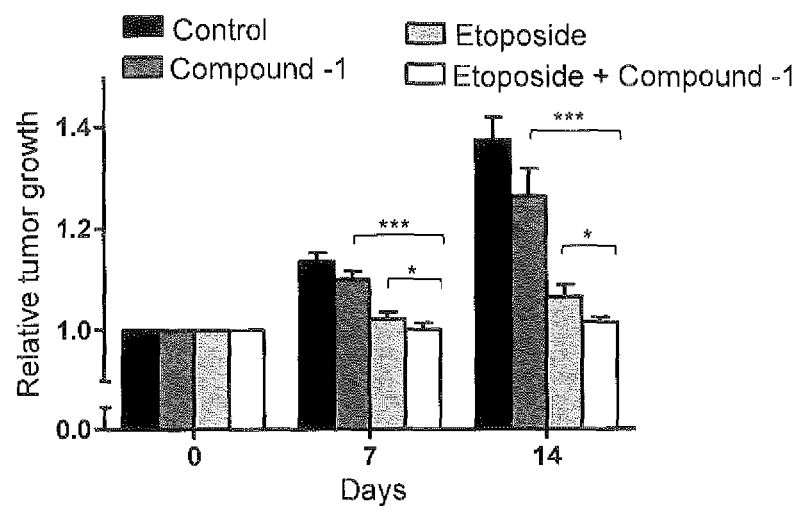
Figure 14:
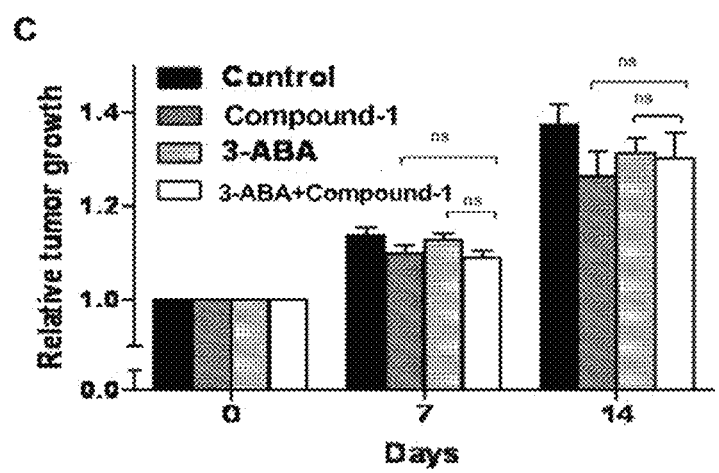
Figures 14D, 14E:
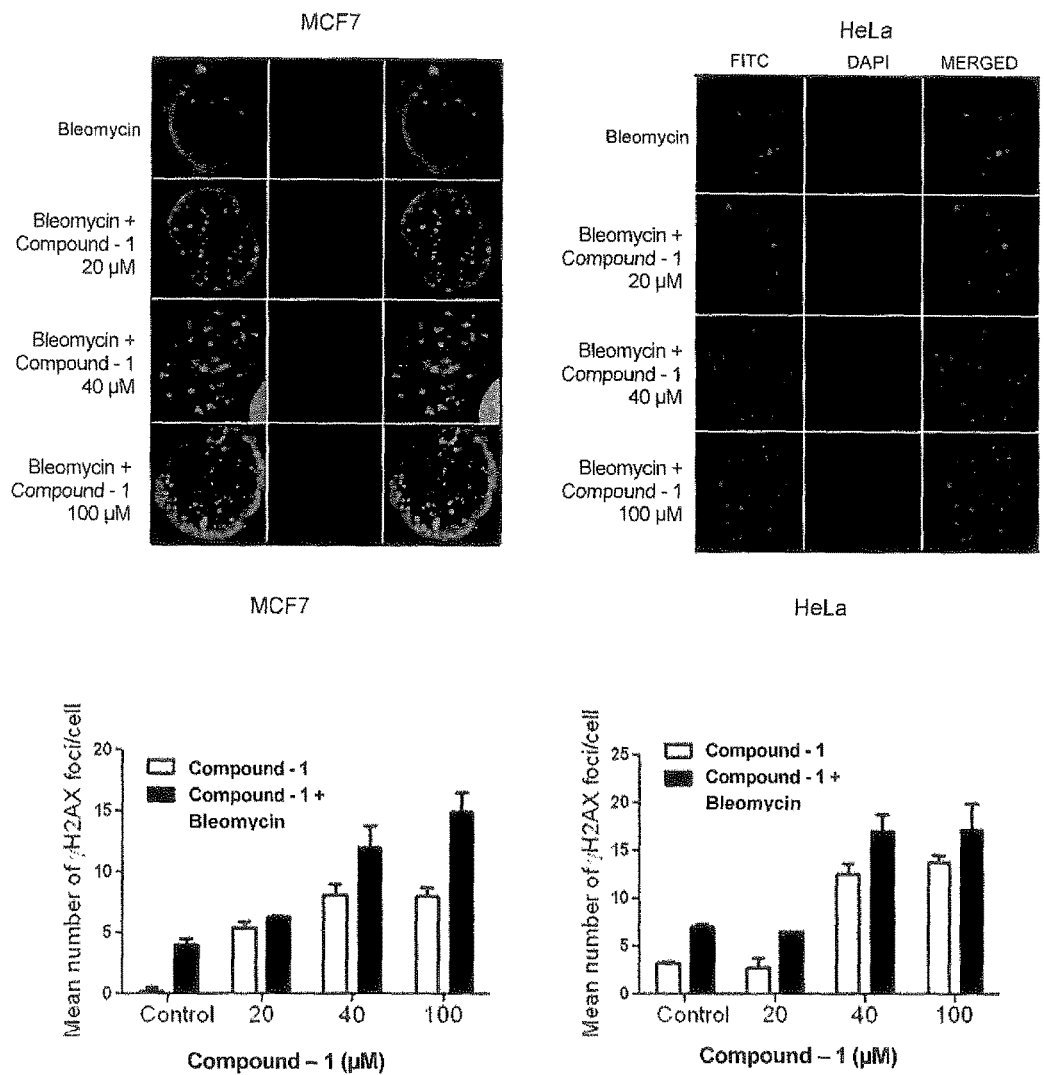

FIG. 14 depicts the evaluation of effect of Compound 1 on tumor progression in mice and proliferation of cancer cells following treatment with radiation and chemotherapeutic agents. A. Comparison of tumor progression induced by DLA cells following treatment with Compound 1 (about 20 mg/kg) for 14 days alone or in conjunction with gamma irradiation (2 Gy). B. Comparison of tumor progression generated by DLA cells following treatment with Compound 1 (about 20 mg/kg) and etoposide (about 10 mg/kg) for 14 days, either alone or together.

FIG. 14 C depicts the comparison of tumor progression generated by DLA cells following treatment with Compound 1 (about 20 mg/kg) and 3-Aminobenzamide (about 10 mg/kg) for 14 days, alone or together.

FIG. 14 D, E depicts the immunofluorescence showing γH2AX foci within the MCF7 (D) or HeLa (E) following treatment with bleomycin (about 5 ng, for about 3 h) alone or after treating with different concentrations of Compound 1 (20, 40 and 100 μM, at about 24 h).

Figure 15:
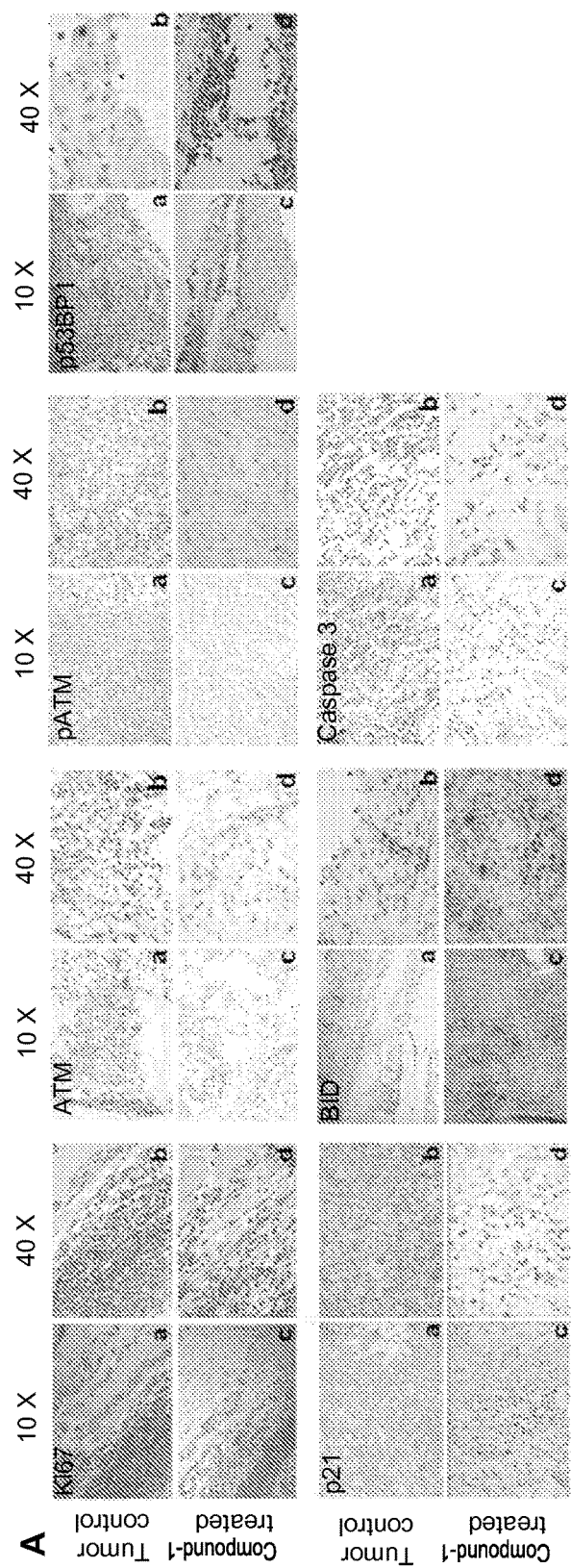
Figure 15:
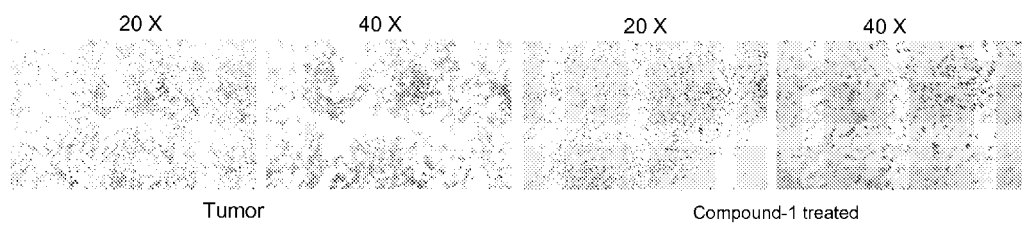
Figure 15:
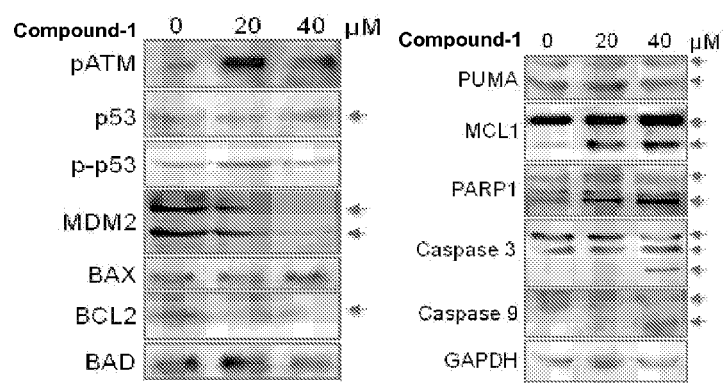
Figure 15:
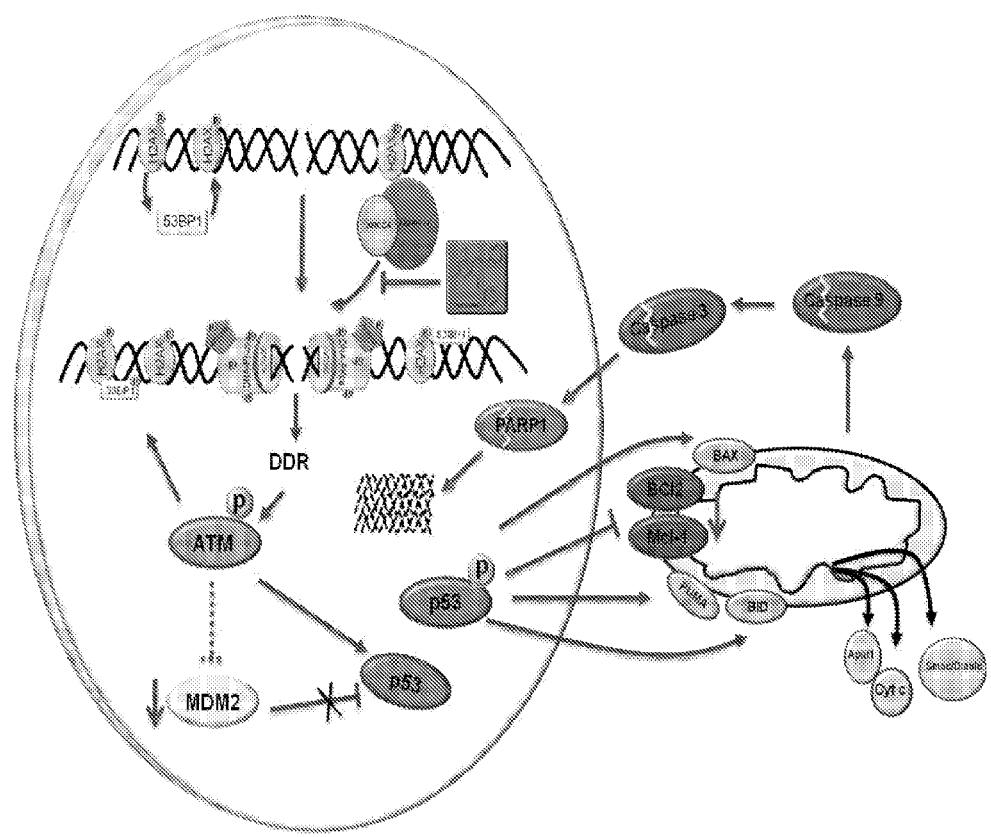

FIG. 15 depicts the analysis of mechanism of Compound 1 induced cytotoxicity in cancer cell lines and tumor models. A. Immunohistochemical studies for evaluation of cell proliferation, DNA repair and apoptotic markers following treatment of Compound 1 to mouse bearing EAC tumors.

FIG. 15 B depicts the tunnel assay showing DNA fragmentation in the nuclei of Compound 1 treated tumor tissues. C. Western blotting for apoptotic and DNA repair markers in MCF7 cells following Compound 1 treatment.

FIG. 15 D depicts the model depicting role of Compound 1 in the inhibition of NHEJ and activation of apoptotic pathway.

DETAILED DESCRIPTION OF THE DISCLOSURE

The present disclosure relates to a compound of formula-I.

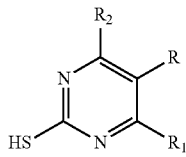

Formula I where, R is selected from a group comprising amine NR'R" and imine —N═C—R'",
$R_1$ is selected from a group comprising amine NR'R" and imine —N═C—R'",
$R_2$ is —OH, and
R', R" and R'" are selected from a group comprising —H, alkyl and aryl or any combination thereof, and its tautomers, isomers, analogs, derivatives and salts thereof, wherein the compound comprises at least one imine group.

In an embodiment of the present invention, R and $R_1$ are optionally interconnected to each other to form a six membered closed ring.

In another embodiment of the present invention, the aryl group is un-, mono-, di- or poly substituted.

In yet another embodiment of the present invention, the imine is

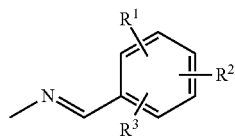

where, $R^1$, $R^2$ and $R^3$ are selected from a group comprising —H, alkyl, alkyloxy, aryl, aryloxy, —F, —Cl, —Br, —I, —$NO_2$, and —OH or any combination thereof.

In still another embodiment of the present invention, the salt is selected from a group comprising sodium salt or potassium salt or a combination thereof.

The present disclosure also relates to a method for preparing a compound of formula-I,

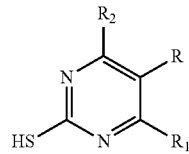

Formula I where, R is selected from a group comprising amine NR'R" and imine —N═C—R'",
$R_1$ is selected from a group comprising amine NR'R" and imine —N═C—R'",
$R_2$ is —OH, and
R', R" and R'" are selected from a group comprising —H, alkyl and aryl or any combination thereof, and its tautomers, isomers, analogs, and derivatives thereof, wherein the compound comprises at least one imine group, comprising steps of:
a) reacting an amine substituted mercaptopyrimidine with a carbonyl compound to obtain a compound of formula I with imine functionality, and
b) optionally, reacting the compound of formula I of step (a), having an additional amine group, with a carbonyl compound by intermolecular or intramolecular fashion, to obtain the compound of formula I with diimine functionality.

In an embodiment of the present invention, R and $R_1$ are optionally interconnected to each other to form a six membered closed ring.

In another embodiment of the present invention, the aryl group is un-, mono-, di- or poly substituted.

In yet another embodiment of the present invention, the imine is

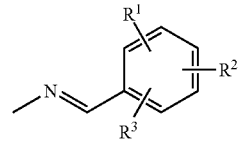

where, $R^1$, $R^2$ and $R^3$ are selected from a group comprising —H, alkyl, alkyloxy, aryl, aryloxy, —F, —Cl, —Br, —I, —$NO_2$, and —OH or any combination thereof.

In still another embodiment of the present invention, the salt is selected from a group comprising sodium salt or potassium salt or a combination thereof.

In still another embodiment of the present invention, the amine substituted mercaptopyrimidine is 4,5-diamino-6-hydroxy-2-mercapto-pyrimidine.

In still another embodiment of the present invention, the carbonyl compound is monocarbonyl compound or dicarbonyl compound.

In still another embodiment of the present invention, the monocarbonyl compound is selected from a group comprising aldehyde, ketone, anhydride and carbonyl halide, preferably benzaldehyde or its derivative of formula III,

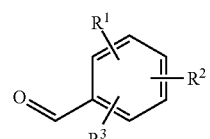

Formula III where $R^1$, $R^2$ and $R^3$ are selected from a group comprising —H, alkyl, alkyloxy, aryl, aryloxy, —F, —Cl, —Br, —I, —$NO_2$, and —OH or any combination thereof.

In still another embodiment of the present invention, the dicarbonyl compound is Indoline-2,3-dione or its derivative of formula IV,

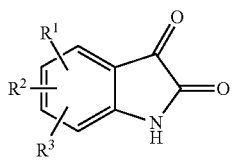

Formula IV where $R^1$, $R^2$ and $R^3$ are selected from a group comprising —H, alkyl, alkyloxy, aryl, aryloxy, —F, —Cl, —Br, —I, —NO$_2$, and —OH or any combination thereof.

In still another embodiment of the present invention, the reacting is carried out in Dimethyl formamide (DMF) solvent in presence of an acid.

In still another embodiment of the present invention, the steps as above further comprises optional steps of isolation, re-crystallization and purification.

The present disclosure also relates to method of arresting DNA double-strand break (DSB) repair, said method comprising act of contacting a compound of formula-I with DNA Ligase for arresting the DNA double-strand break (DSB) repair.

In an embodiment of the present invention, the DNA Ligase is DNA Ligase IV.

In another embodiment of the present invention, the DNA double-strand break (DSB) repair is carried out by non-homologous end joining (NHEJ) pathway.

In yet another embodiment of the present invention, the non-homologous end joining (NHEJ) pathway comprises enzyme DNA Ligase IV.

In still another embodiment of the present invention, the compound of structural formula-I inhibits activity of the DNA Ligase IV.

In still another embodiment of the present invention, the inhibition is carried out by binding of the compound to DNA binding domain of the DNA Ligase IV.

In still another embodiment of the present invention, the binding results in the arrest of the DNA double-strand break (DSB) repair.

In an embodiment of the present disclosure, potent inhibitors of non-homologous DNA End Joining (NHEJ) pathway are disclosed. The said inhibitors are Compounds 1-16, which block the NHEJ pathway and thereby, prevent DNA double-strand break (DSB) repair.

In another embodiment of the present disclosure, inhibition of NHEJ pathway is carried out by Compound 1. The said inhibition is carried out by inhibiting the joining of various DSBs in a cell-free repair system. Compound 1 blocks joining by purified Ligase IV, by interfering with its binding to DNA, but not of T4 DNA Ligase or Ligase I. Importantly, inhibition is restored by addition of Ligase IV/XRCC4 complex Inhibition of NHEJ by Compound 1 within cells leads to accumulation of unrepaired DSBs, thereby activating intrinsic pathway of apoptosis.

In another embodiment of the present disclosure, inhibition of double-strand break repair by Compound 1 is used as a therapy for cancer. Compound 1 impedes tumor progression in different mice models and when co-administered with existing DSB inducing therapeutic modalities, enhance their sensitivity significantly. Most commonly used cancer therapeutic procedures include radiation and chemotherapy. Both these modalities generate DNA double strand breaks as intermediate for their action. Cancer cells responsible for tumor relapse and resistance are found to have hyperactive DSB repair. Hence, combining inhibitors of DSB repair (Compound 1) proves to be a very effective way of combating cancer. The present disclosure showcases that the treatment of Compound 1 along with other modalities increases the susceptibility of the cancer cells and decreases the effective dose of radio and chemotherapy. Therefore, Compound 1 which targets NHEJ by disrupting joining of DSBs by Ligase IV is employed for the management of cancer. Based on the choice of DSB repair pathways, in a particular type of cancer, a target based therapy is developed. Further, as described above, the use of DNA repair inhibitors along with existing chemo and radio-therapeutics improve efficacy of treatment by many fold.

Downregulation of NHEJ in cancer cells leads to elevated sensitivity to radiation and chemotherapeutic agents. Therefore, the present disclosure discloses the inhibition of NHEJ as one of the several ways to make cancer cells hypersensitive to radiations and other DSB inducing chemotherapeutic agents. The present disclosure uses Ligase IV as a target, since it is the critical enzyme involved in NHEJ. Specifically, targeting of the DNA binding domain of Ligase IV is carried out such that it reduces its binding affinity for DSBs and deters its physiological function.

Additional embodiments and features of the present disclosure will be apparent to one of ordinary skill in art based upon description provided herein. The present disclosure is further elaborated with the following examples and figures. However, the examples and the figures should not be construed to limit the scope of the present disclosure.

Example 1

Ligase IV Inhibitors:
The following are the inhibitors of Ligase IV activity—

COMPOUND 1

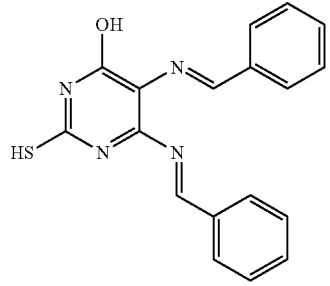

(5E,6E)-5,6-bis(benzylideneamino)-2-mercaptopyrimidin-4-ol

COMPOUND 2

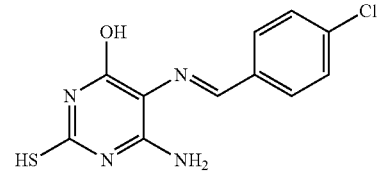

(E)-5-(4-chlorobenzylideneamino)-6-amino-2-mercaptopyrimidin-4-ol (5E,6E)-5,6-bis(4-chlorobenzylideneamino)-2-mercaptopyrimidin-4-ol

COMPOUND 3

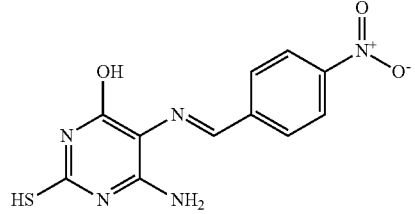

(E)-5-(4-nitrobenzylideneamino)-6-amino-2-mercaptopyrimidin-4-ol

COMPOUND 7

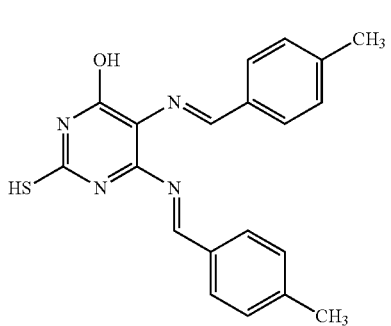

(5E,6E)-5,6-bis(4-methylbenzylideneamino)-2-mercaptopyrimidin-4-ol

COMPOUND 4

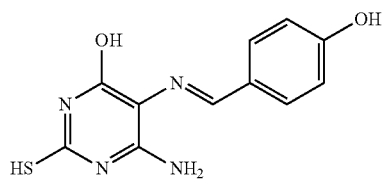

(E)-5-(4-hydroxybenzylideneamino)-6-amino-2-mercaptopyrimidin-4-ol

COMPOUND 8

2-mercapto-10H-indolo[3,2-g]pteridin-4-ol

COMPOUND 9

COMPOUND 5

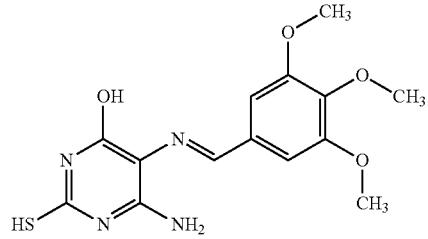

(E)-5-(3,4,5-trimethoxybenzylideneamino)-6-amino-2-mercaptopyrimidin-4-ol

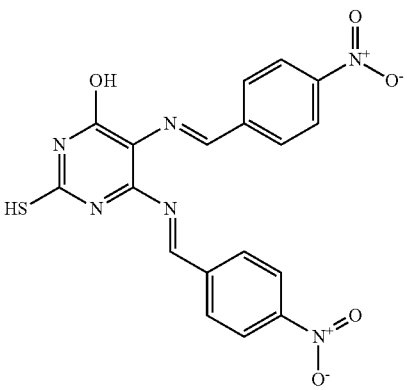

(5E,6E)-5,6-bis(4-nitrobenzylideneamino)-2-mercaptopyrimidin-4-ol

COMPOUND 10

COMPOUND 6

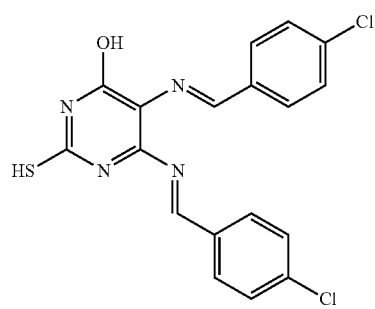

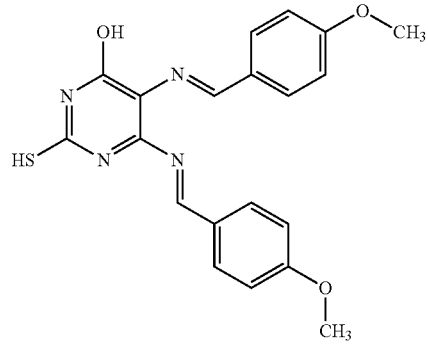

(5E,6E)-5,6-bis(4-methoxybenzylideneamino)-2-mercaptopyrimidin-4-ol

COMPOUND 11

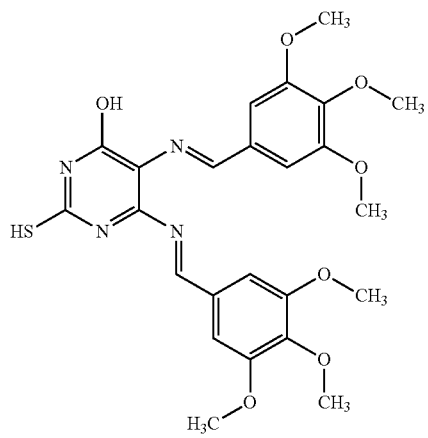

(5E,6E)-5,6-bis(3,4,5-trimethoxybenzylideneamino)-2-mercaptopyrimidin-4-ol

COMPOUND 12

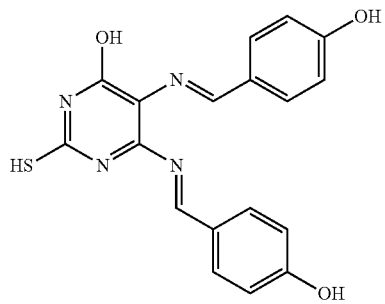

(5E,6E)-5,6-bis(4-hydroxybenzylideneamino)-2-mercaptopyrimidin-4-ol

COMPOUND 13

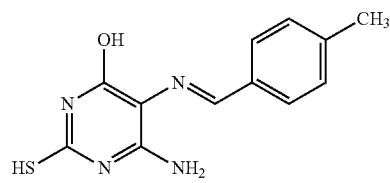

(E)-5-(4-methylbenzylideneamino)-6-amino-2-mercaptopyrimidin-4-ol

COMPOUND 14

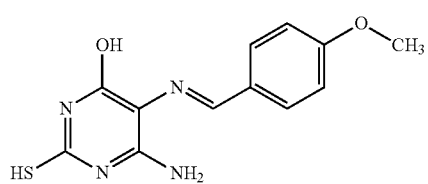

(E)-5-(4-methoxybenzylideneamino)-6-amino-2-mercaptopyrimidin-4-ol

COMPOUND 15

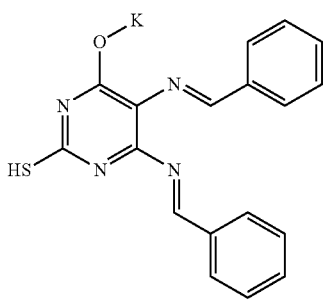

Sodium 5,6-bis((E)-benzylideneamino)-2-mercaptopyrimidin-4-olate

COMPOUND 16

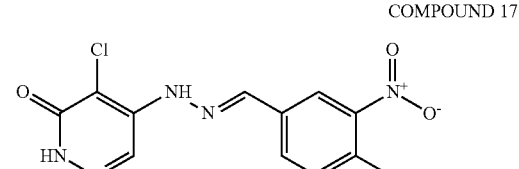

Potassium 5,6-bis((E)-benzylideneamino)-2-mercaptopyrimidin-4-olate

COMPOUND 17

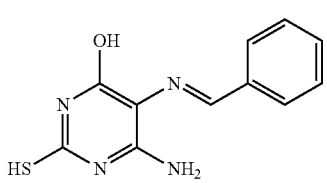

COMPOUND 18

Example 2

Synthesis and Characterization of Compounds 2-5, 13 and 14

A suspension of 5,6-diamino-4-hydroxy-2-mercaptopyrimidine (0.05 mol) and benzaldehyde/substituted benzaldehyde (0.05 mol) in dimethyl formamide (30 ml) and acetic acid (10 ml) is stirred at room temperature for overnight. Contents of the reactions are added to ice cold water, and separated solid is filtered, washed with water and recrystallised from dimethyl formamide-ethanol. The reaction scheme is as follows—

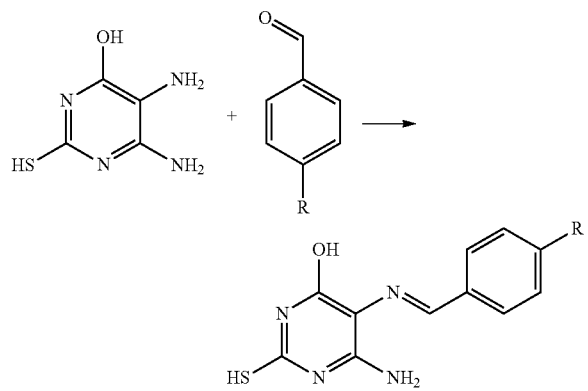

Where, R=Cl (Compound 2), NO$_2$ (Compound 3), OH (Compound 4), (OCH$_3$)$_3$ [Compound 5], CH$_3$ (Compound 13), OCH$_3$ (Compound 14).

Compound 2

Yield 60%. Nature: Amorphous powder. Melting point: >300° C. Solubility: soluble in dimethyl formamide (DMF), dimethyl sulfoxide (DMSO). Partially soluble in ethanol. Insoluble in chloroform (CHCl$_3$). IR: 3436, 3317, 3076, 2955, 2912, 1628, 1536, 1432. $^1$H NMR δ(ppm): 11.98 (s, 1H), 11.85; (s, 1H), 9.62; (s, 1H), 7.92; (d, 2H, J=8.4 Hz), 7.45; (d, 2H, J=8.4 Hz), 6.83; (s, br, 2H, NH$_2$). +ESI: 281.1 (M). Rf: 0.66.

Compound 3

Yield 70%. Nature: Amorphous powder. Melting point: >320° C. Solubility: soluble in dimethyl formamide (DMF), dimethyl sulfoxide (DMSO). Partially soluble in ethanol. Insoluble in chloroform (CHCl$_3$). IR: 3470, 3356, 3130, 2977, 1604, 1525, 1425, 1338. $^1$H NMR δ(ppm): 12.06; (s, 1H), 11.92; (s, 1H), 9.73; (s, 1H), 8.22; (d, 2H, J=8.8 Hz), 8.16; (d, 2H, J=8.8 Hz), 6.97; (s, br, 2H, NH$_2$). +ESI: 290.1 (M-1). Rf: 0.63

Compound 4

Yield 40%. Nature: Amorphous powder. Melting point: >320° C. Solubility: soluble in dimethyl formamide (DMF), dimethyl sulfoxide (DMSO). Partially soluble in ethanol. Insoluble in chloroform (CHCl$_3$). IR: 3298, 3177, 2920, 2853, 1617, 1354, 1267. $^1$H NMR δ(ppm): 11.99 (s, 1H), 11.21; (s, 1H), 9.54; (s, 1H), 7.70; (d, 2H, J=8.8 Hz), 7.60; (s, br, 1H), 6.80; (d, 2H, J=8.8 Hz), 6.53; (s, br, 2H, NH$_2$). +ESI: 262.1 (M-1). Rf: 0.52.

Compound 5

Yield 50%. Nature: Crystalline powder. Melting point: 315° C. Solubility: soluble in dimethyl formamide (DMF), dimethyl sulfoxide (DMSO). Partially soluble in ethanol. Insoluble in chloroform (CHCl$_3$). IR: 3437, 3329, 3129, 2992, 2836, 1618, 1548, 1424, 1324, 1233. $^1$H NMR δ(ppm): 11.96; (s, 1H), 11.76; (s, 1H), 9.58; (s, 1H), 7.15; (s, 2H), 6.74; (s, br, 2H, NH$_2$), 3.88; (s, 6H, —2OCH$_3$), 3.68; (s, 3H, —OCH$_3$). +ESI: 337.1 (M+1). Rf: 0.75.

Compound 13

Yield 51%. Nature: Amorphous powder. Solubility: soluble in dimethyl formamide (DMF), dimethyl sulfoxide (DMSO). Partially soluble in ethanol. Insoluble in chloroform (CHCl$_3$).

IR: 3445, 3297, 3138, 3059, 2988, 1600, 1543, 1433, 1352, 1236. +ESI: 261.1 (M+1). Rf: 0.66

Compound 14

Yield 50%. Nature: Amorphous powder. Solubility: soluble in dimethyl formamide (DMF), dimethyl sulfoxide (DMSO). Partially soluble in ethanol. Insoluble in chloroform (CHCl$_3$).

IR: 3501, 3387, 3157, 3065, 1652, 1619, 1510, 1428, 1378, 1239. +ESI: 277.1 (M+1). Rf: 0.65

Example 2

Synthesis and Characterization of Compounds 1, 6, 7, 9-12

A suspension of 6-amino-5-(benzylideneamino)-2-sulfanylpyrimidin-4-ol (0.05 mol) and respective benzaldehyde (0.05 mol) in dimethyl formamide (30 ml) and acetic acid (10 ml) is refluxed for 3 hours. After cooling, contents of the reactions are added to ice cold water, and separated solid is filtered, washed with water. The reaction scheme is as follows—

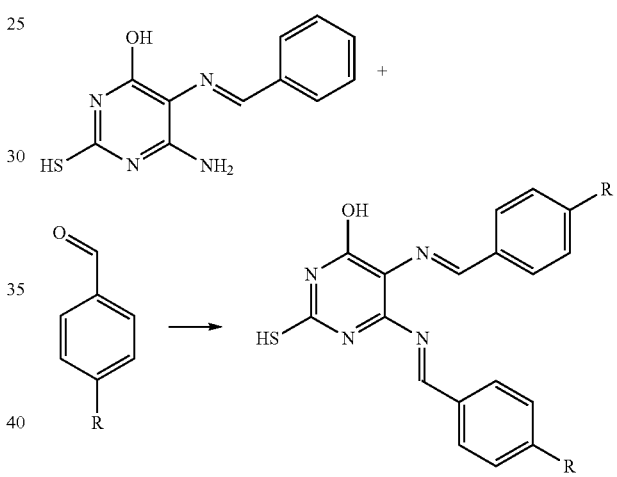

Where, R=H (Compound 1), Cl (Compound 6), CH$_3$ (Compound 7), NO$_2$ (Compound 9), OCH$_3$ (Compound 10), 3,4,5-(OCH$_3$)$_3$ (Compound 11), OH (Compound 12).

Compound 1

Recrystallized from ethyl acetate-Hexane. Yield 42%. Nature: Amorphous powder. Melting point: 221-225° C. Solubility: soluble in dimethyl formamide (DMF), dimethyl sulfoxide (DMSO). Partially soluble in ethanol. Insoluble in chloroform (CHCl$_3$). IR: 3195, 3062, 1612, 1558, 1360, 1149. $^1$H NMR δ(ppm): 7.53-7.36; (7H, m, ar), 7.88-7.86; (2H, m, ar), 8.11-8.08; (1H, m, ar), 9.64; (2H, m, ar), 11.97; (1H, s, —OH), 12.80 (1H, s, —SH). -ESI: 333 (M-1). Rf: 0.53.

Compound 6

Yield 58%. Nature: Amorphous powder. Melting point: 260-262° C. Solubility: soluble in dimethyl formamide (DMF), dimethyl sulfoxide (DMSO). Partially soluble in ethanol. Insoluble in chloroform (CHCl$_3$). IR: 3279, 3059, 2917, 1641, 1596, 1408, 1361, 1145, 1097. $^1$H NMR δ(ppm): 12.08; (1H, s, br, —SH), 11.95; (s, 1H, —OH), 7.83; (2H, d, J=8), 7.58; (1H, s), 7.45; (2H, d, J=8), 7.42; (2H, d, J=8), 7.30; (2H, d, J=8), 6.02; (1H, s, ar). +ESI: 403 (M). Rf: 0.66.

Compound 7

Yield 55%. Nature: Amorphous powder. Melting point: 181-183° C. Solubility: soluble in dimethyl formamide (DMF), dimethyl sulfoxide (DMSO). Partially soluble in ethanol. Insoluble in chloroform ($CHCl_3$). IR: 3205, 3104, 2918, 1604, 1560, 1436, 1349, 1235, 1146. $^1$H NMR δ(ppm): 11.97; (1H, s, br, —SH), 11.86; (1H, s, —OH), 7.72; (2H, d, J=8), 7.39; (1H, s), 7.18-7.11; (6H, m, ar), 5.94; (1H, s, ar), 2.28; (3H, s, CH3), 2.22; (3H, s, CH3). -ESI: 361.1 (M). Rf: 0.77.

Compound 9

Yield 52%. Nature: Amorphous powder. Solubility: soluble in dimethyl formamide (DMF), dimethyl sulfoxide (DMSO). Partially soluble in ethanol. Insoluble in chloroform ($CHCl_3$).

IR: 3358, 3217, 3040, 2879, 1692, 1604, 1521, 1346, 1180. -ESI: 423.2; (M−1). Rf: 0.70

Compound 10

Yield 52%. Nature: Amorphous powder. Solubility: soluble in dimethyl formamide (DMF), dimethyl sulfoxide (DMSO). Partially soluble in ethanol. Insoluble in chloroform ($CHCl_3$).

IR: 3455, 3053, 2899, 1608, 1512, 1461, 1253. +ESI: 395.5 (M+1). Rf: 0.65

Compound 11

Yield 52%. Nature: Amorphous powder. Solubility: soluble in dimethyl formamide (DMF), dimethyl sulfoxide (DMSO). Partially soluble in ethanol. Insoluble in chloroform ($CHCl_3$).

IR: 3469, 3337, 3144, 3076, 2948, 2902, 1622, 1549, 1435, 1354, 1239. +ESI: 515.7 (M+1). Rf: 0.68

Compound 12

Yield 52%. Nature: Amorphous powder. Solubility: soluble in dimethyl formamide (DMF), dimethyl sulfoxide (DMSO). Partially soluble in ethanol. Insoluble in chloroform ($CHCl_3$).

IR: 3437, 3329, 3129, 2992, 2836, 1618, 1548, 1424, 1324, 1233. +ESI: 365.1 (M−1). Rf: 0.63

Figure 1:
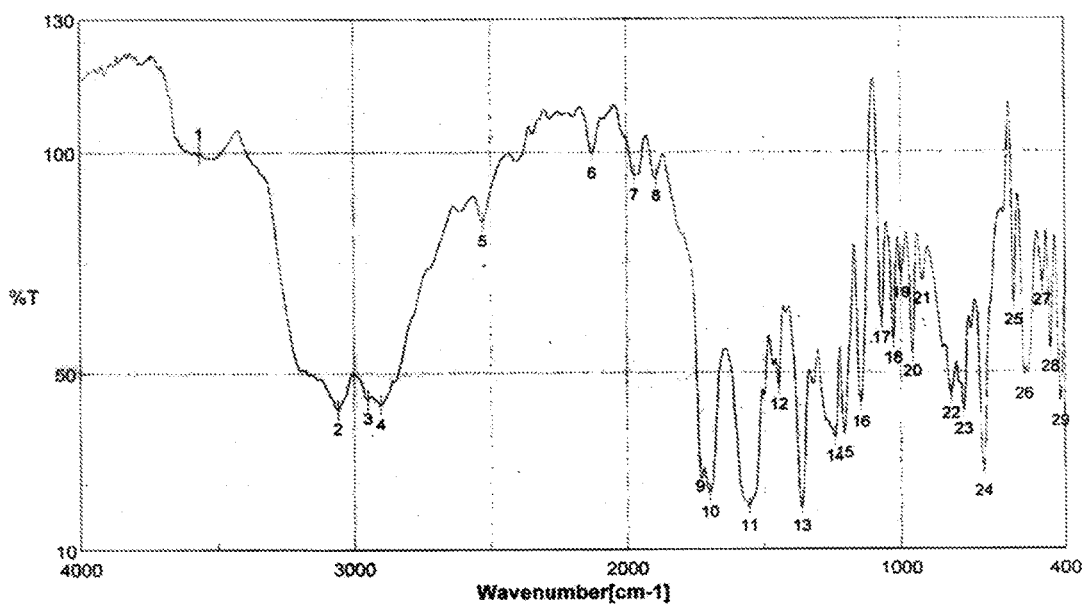
Figure 1B:
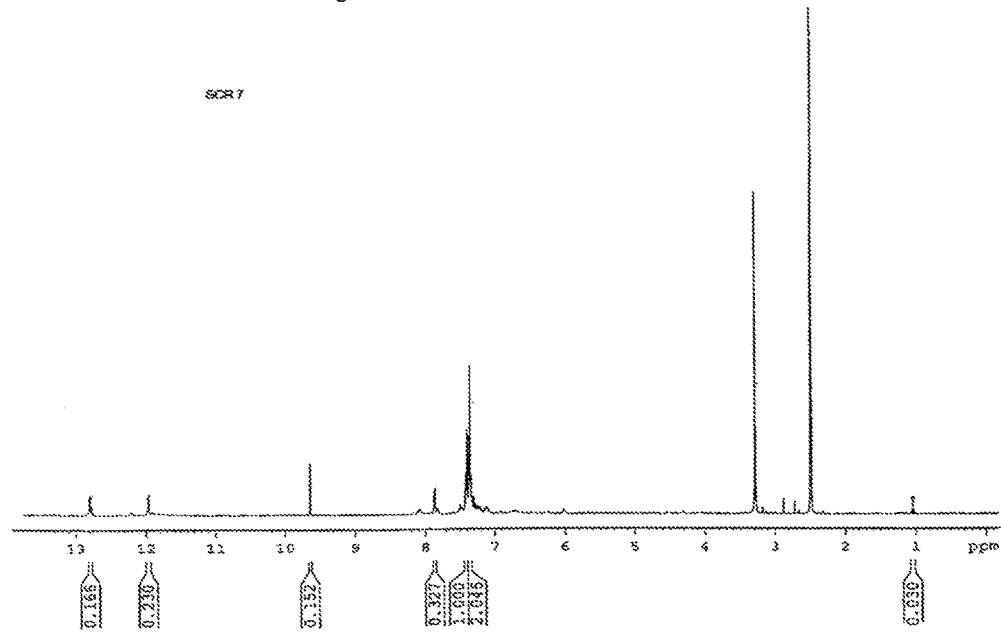
Figure 1C:
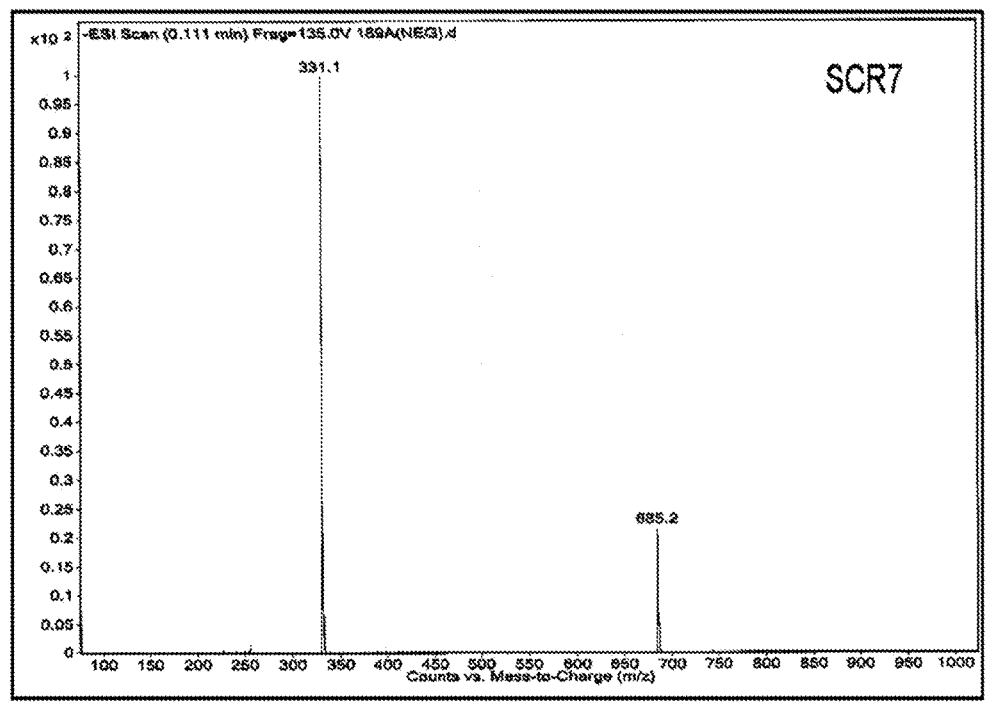
Figure 1D:
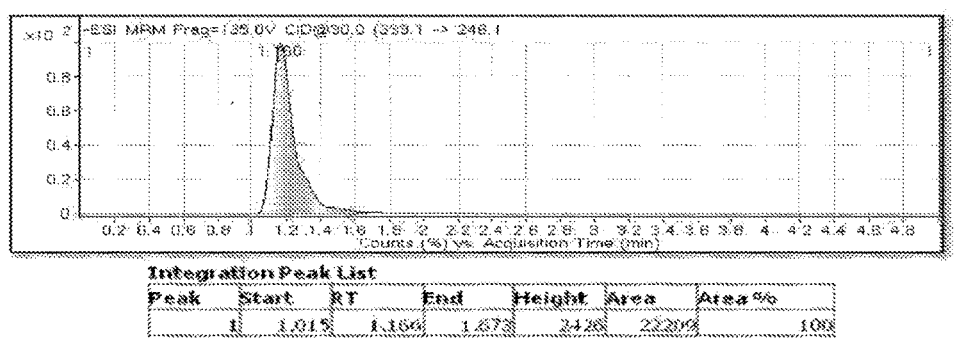

FIG. 1 depicts the characterization of compound 1. A. Characterization of Compound 1 by IR spectroscopy. B. NMR spectrum of Compound 1. C and D. LC MS/MS spectrum (D) with its chromatogram (E), indicating retention time and purity of the Compound 1.

Example 3

Synthesis and Characterization of Compound 8:

A suspension of 5,6-diamino-4-hydroxy-2-mercaptopyrimidine (0.05 mol) and indoline-2,3-dione (0.05 mol) in dimethyl formamide (30 ml) and acetic acid (10 ml) is refluxed for 3 hours. After cooling, contents of the reactions are added to ice cold water, and separated solid is filtered, washed with water and recrystallised from dimethyl formamide-ethanol. The reaction scheme is as follows—

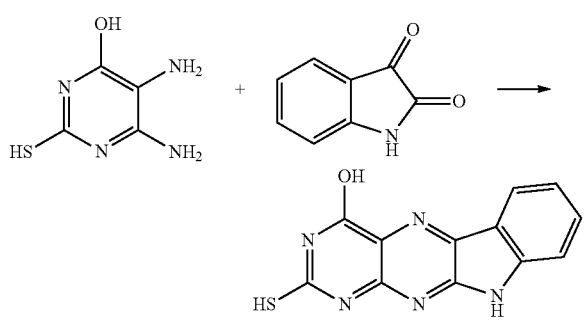

Compound 8

Yield 60%. Nature: Amorphous powder. Melting point: >320° C. Solubility: soluble in dimethyl formamide (DMF), dimethyl sulfoxide (DMSO). Partially soluble in ethanol. Insoluble in chloroform ($CHCl_3$). IR: 3505, 3136, 3098, 1674, 1564, 1358, 1200, 1155. $^1$H NMR δ(ppm): 13.26; (1H, s), 12.66; (2H, d, J=8 Hz), 8.23; (1H, d, J=8 Hz), 7.64; (1H, t, J=16 Hz), 7.57; (1H, d, J=8 Hz), 7.39; (1H, t, J=16 Hz). +ESI: 270.1 (M+1). Rf: 0.88.

Example 4

Synthesis of Compounds 15 and 16:

Compound 1 is added to alcoholic sodium/potassium hydroxide (1:1 respectively) and stirred to homogeneous thin paste which soon liquefied to a deep yellow color solution. The liquid is dried in a current of air at 40° C. The dried mass is dissolved in cold water and then filtered. The filtrates containing sodium/potassium salt of Compound 1 is evaporated to dryness and finally in a desiccator to constant weights. The reaction scheme is as follows—

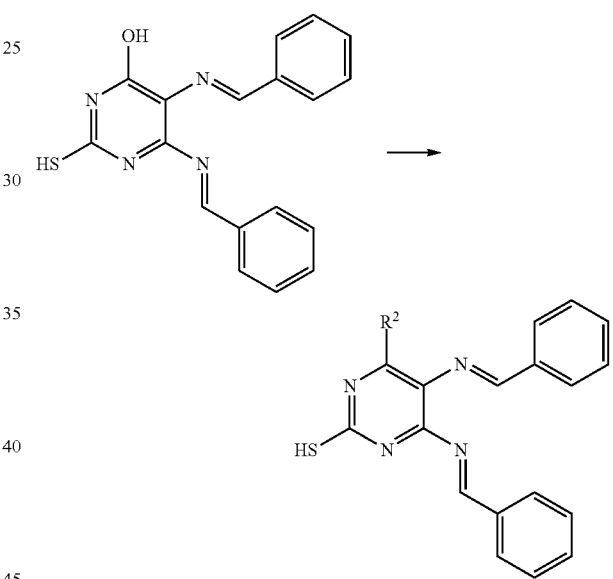

Where, $R^2$=ONa (Compound 15), OK (Compound 16).

Compound 15

Nature: Amorphous powder. Solubility: Soluble in water. +ESI MS: 357.1 (M+1).

Compound 16

Nature: Amorphous powder. Solubility: Soluble in water. +ESI MS: 370.9 (M−1).

Example 5

Compound 1 as an inhibitor of DNA end Joining

Figure 2B:
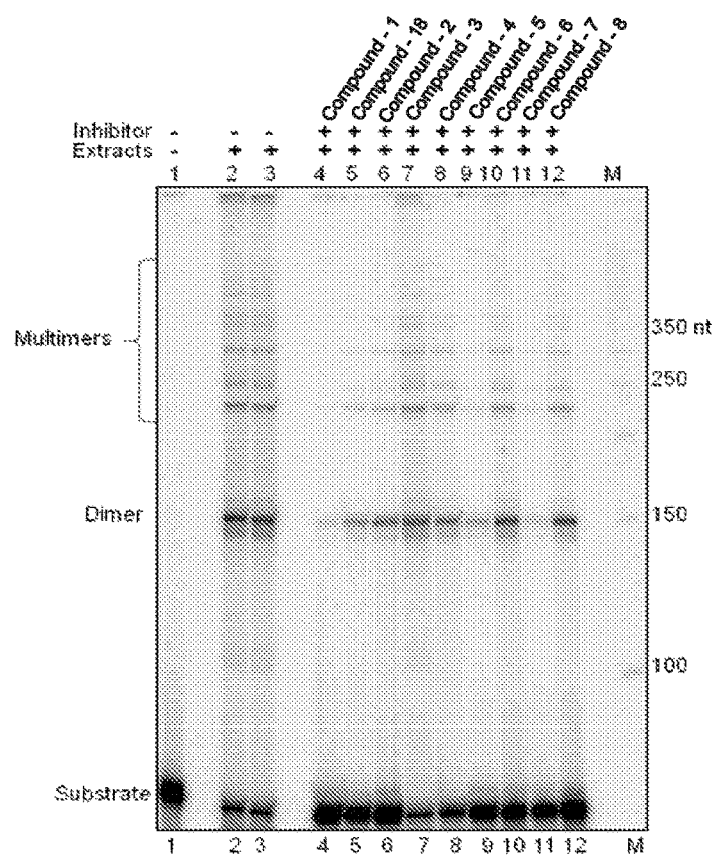
FIG. 2B depicts comparison of the effect of potential Ligase IV inhibitors on DNA end joining C. Quantification of the joining efficiency.
Figure 2C:
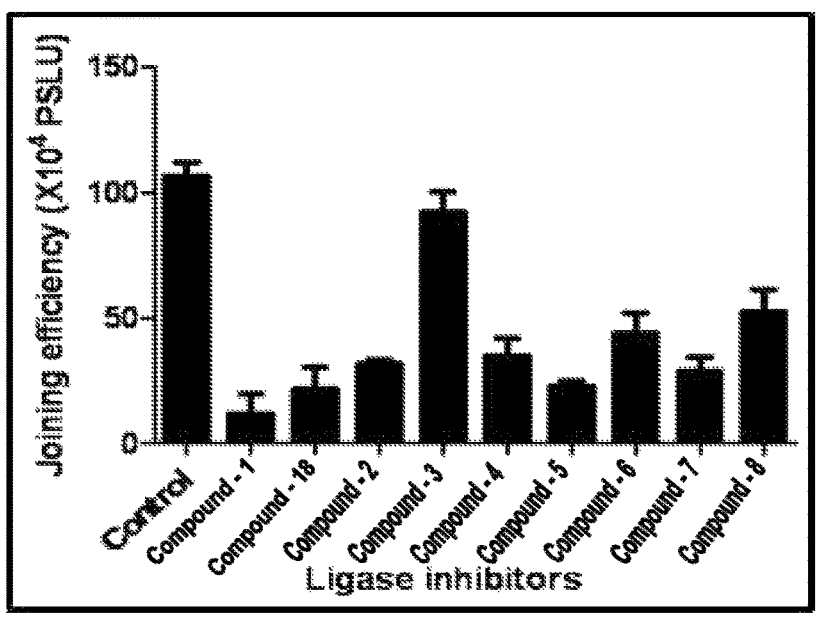
FIG. 2D depicts the results of agarose gel electrophoresis when pUC18 linearized by EcoRI digestion is incubated with indicated concentrations of either Compound 1 or ethidium bromide.

NHEJ assays (FIG. 2) are carried out and effect of Ligase IV inhibitors (Compounds 1-8) on DNA end joining is tested. About 0.5 μg of cell-free extracts prepared from rat testes are pre-incubated with inhibitors (about 150 μM) for about 30 min at about 25° C. and subjected to End Joining with [g-32¬ P] ATP end-labeled oligomeric DNA substrate (75 bp) containing 4 nt overhangs at 5' ends (about 2 h at 25° C.). In the case of vehicle control, DMSO is used. Compound 17 and 18 are used as control. The reaction products are purified and resolved on about 8% denaturing polyacrylamide gel. Addition of putative Ligase IV inhibitors [Compound 1-8] results in inhibition of DNA end joining to different extents and the quantification of joining efficiency of various inhibitors proves Compound 1 to be the most potent inhibitor of DNA Ligase IV (FIG. 2H).

FIG. 2 depicts the NHEJ assay and study of joining efficiency. A. Schematic representation of NHEJ assay and substrates containing DSBs. B. Comparison of the effect of potential Ligase IV inhibitors on DNA end joining. The joined products are indicated. "M" represents [g-32¬ P] ATP end-labeled 50 by ladder. C. Quantification of the joining efficiency. The bar graph shows mean±standard error mean (SEM) from three independent experiments. "PSLU" is "photostimulated luminescence unit". D. pUC18 linearized by EcoRI digestion is incubated with indicated concentrations of either Compound 1 or ethidium bromide at about 37° C. for about 15 min. Products are resolved on 1% agarose gel and visualized. Ethidium bromide is used as a positive control for the intercalation assay.

FIG. 3 depicts the list of oligomers used for the NHEJ assays.

Example 6

Compound 1 and Compound 15 Mediated Inhibition of DNA End Joining of Various Types of DSBs A cell-free repair assay system derived from rat testes is used to study the effect of Compound 1 and Compound 15 on NHEJ. Compound 1 and Compound 15 inhibits end joining (EJ) irrespective of type and configurations of DSB (FIG. 4 (I) B-G and FIG. 4 (II) B-D).

FIG. 4 (I) depicts the structural and functional characterization of putative Ligase IV inhibitor Compound 1 using DNA substrates possessing various DSBs. A. Chemical structure of Compound 1 [5,6-bis(benzylideneamino)-2-mercapto-pyrimidin-4-ol]. B. Effect of Compound 1 on joining of 5' compatible ends. [$\gamma$-$^{32}$P]ATP labeled oligomeric DNA is incubated with rat testes extracts, which is pre-incubated with Compound 1. The reaction products are resolved on 8% denaturing PAGE. "M" represents [$\gamma$-$^{32}$P] ATP end-labeled 50 by ladder. C-E. Effect of Compound 1 on EJ of 5'-5' noncompatible (E), 5'-3' noncompatible (F) and blunt (G) ends. F. Effect of Ligase I inhibitor, Compound 17 on joining of 5' compatible ends catalysed by testicular extracts. G. Effect of Compound 1 on plasmid based EJ. Extracts (about 0.5 μg) are pre-incubated with Compound 1 (about 200 μM), added to linearized pDNA and products are resolved on an agarose gel (1%). "M" is a 2 log DNA ladder.

FIG. 4 (II) depicts the structural and functional characterization of Compound 21. A. Chemical structure of Compound 21. B. Effect of Compound 21 on the joining of 5' compatible ends. [$\gamma$-$^{32}$P]ATP labeled oligomeric DNA is incubated with rat testes extracts, following pre-incubation with Compound 21. The reaction products are purified and resolved on 8% denaturing PAGE. "M" represents 50 by ladder. C and D. Effect of Compound 21 on the joining catalyzed by purified Ligase IV/XRCC4 (C) and Ligase III/XRCC1 (D) on joining of 5' compatible ends and nicked substrates, respectively.

FIG. 8 depicts the effect of Compound 1 on joining efficiency of compatible ends when increasing concentrations of DNA substrates are used. A. Gel profile showing competition studies using increasing concentrations of DNA and Compound 1 for binding site on Ligase IV. Protein (about 30 fmol) is pre-incubated with Compound 1 (about 150 μM) followed by addition of increasing concentrations of DNA (1, 2, 4, 6 and 8 nM). Reaction products are purified and resolved on denaturing PAGE. B. Image is analyzed and quantitated using Multi Gauge (ver 3.0) software and presented as a bar diagram.

Example 7

Interference of Compound 1 with Ligase IV Activity and Inhibition of NHEJ

Compound 1 blocks joining by purified Ligase IV by interfering with its binding to DNA, but not of T4 DNA Ligase or Ligase I, when equimolar concentration of protein is used. In order to further validate the specificity of Compound 1 with respect to NHEJ in cell-free extracts, Ligase IV complementation experiments are performed. Results confirm that addition of Compound 1 to the testicular extracts abrogates end joining (FIG. 6E, lane 3, FIG. 6F). Interestingly, addition of purified Ligase IV/XRCC4 to the reaction restores joining for all the ends including DSBs with noncompatible ends (FIG. 6E, F). These results indicates that purified Ligase IV/XRCC4 complex complements the joining of noncompatible ends, firmly establishing Compound 1 as an inhibitor of NHEJ.

FIG. 5 depicts the overexpression and purification of Ligase IV/XRCC4, DBD Ligase IV, Ligase I and Ligase III. A. Schematic representation of strategy used for the purification of Ligase IV/XRCC4. B-E. SDS-PAGE profile of eluted fractions of purified Ligase IV/XRCC4 (B), DBD of Ligase IV (C) Ligase I (D), Ligase IIIα/XRCC1 (E). Alternate fractions are loaded on the SDS-PAGE and visualized by silver staining. Purest fractions are pooled, dialyzed and used for the assays. In the case of Ligase I and III western confirming presence of the protein is also shown. In panels B-E, lanes 1 and 2 indicate two different purified fractions. W is wash.

FIG. 6 depicts the effect of Compound 1 on DNA end joining catalysed by purified Ligase IV/XRCC4 complex and analysis of its specificity. A. Western blotting showing presence of Ligase IV/XRCC4 in eluted fractions. W is wash, 1 and 2 are different fractions. B. Comparison of effect of Compound 17 and Compound 1 on DSB joining of 5' compatible ends catalysed by purified Ligase IV/XRCC4 complex (about 60 fmol). Concentrations of inhibitors used are indicated. For other details, FIG. 4 legend can be referred. C. Bar diagram representing quantification of effect of Compound 1 on EJ of 5' complementary end catalysed by purified Ligase IV/XRCC4 complex or T4 DNA ligase. D. Bar diagram representing quantification of effect of Compound 1 on ligation of a nick on a double-stranded oligomeric DNA substrate catalysed by purified Ligase I or Ligase III. E. Complementation of Compound 1 mediated inhibition of NHEJ by purified Ligase IV/XRCC4 complex. Ligase IV inhibition is carried out by addition of Compound 1 (about 150 μM) to testicular extracts. Radiolabeled oligomeric DNA substrates containing 5' compatible termini are then added to the reaction along with increasing concentrations of purified Ligase IV/XRCC4 complex (30, 60 and 120 fmol) and products are resolved on a PAGE. F. Bar diagram representing quantification of the complementation experiment performed on 5'-5' and 5'-3' noncomplementary ends. In all panels quantification of EJ based on 3 independent experiments is represented as mean±SEM.

Example 8

Binding of Compound 1 to the DNA Binding Domain (DBD) of Ligase IV and Interference with the Binding of Ligase IV to DSBs Addition of purified Ligase IV/XRCC4 to the KU:DNA complex results in a supershift indicating its interaction with the KU bound DNA (FIG. 7B, lanes 4,5; FIG. 7C, lane 3).

Interestingly, a dose-dependent reduction in the band corresponding to the supershift upon addition of increasing concentrations of Compound 1 is observed indicating unavailability of Ligase IV to interact with DNA. In order to exclude the effect of interacting partner XRCC4 and determine the domain responsible for the binding of Compound 1 to Ligase IV, CD spectroscopic studies are performed. Results (FIG. 7D-1 and FIG. 7D-2) show a clear shift in the spectrum, upon addition of Compound 1 to Ligase IV or DBD as compared to respective proteins alone.

FIG. 7 depicts the evaluation of Compound 1 binding to the DNA binding domain of Ligase IV and its effect on binding to DSBs. A. Western blot analysis of KU70 and KU80 proteins in purified fractions. W is wash, 1, 2 and 3 are different fractions. B. Binding of KU proteins to DNA breaks. [−$\gamma^{32}$P]ATP end-labeled oligomeric DNA substrate containing DSB is incubated for about 30 min on ice with purified KU or Ligase IV/XRCC4 complex. For Ligase IV/XRCC4 supershift, first KU and DNA are incubated followed by addition of Ligase IV/XRCC4 (about 60 fmol). Reaction mixture is resolved on 1-6% native gradient PAGE. C. Analysis of effect of Compound 1 on Ligase IV/XRCC4 complex binding to DNA. After preincubation of KU with DNA substrates, Ligase IV/XRCC4 complex (about 60 fmol) and increasing concentrations of inhibitor (10, 50, 100, 200, 500 and 700.mu.M) are added, incubated and products are resolved on a gradient native PAGE. D-1 and D-2. CD spectroscopy to evaluate structural changes in Ligase IV and DBD upon binding to Compound 1. Ligase IV or DBD of Ligase IV alone is overexpressed, purified and presence is confirmed by western blotting. CD spectra are obtained at a wavelength of 200-260 nm for Ligase IV or DBD along with Compound 1.

Example 9

Compound 1 Mediated Inhibition of NHEJ within Cancer Cells and Generation of Unrepaired DSBs Based on the above results, it is observed that the abrogation of innate NHEJ results in the accumulation of unrepaired DSBs at genome level. To test this, breast cancer (MCF7) and cervical cancer (HeLa) cell lines are treated with Compound 1 and immunofluorescence studies are performed using anti-γH2AX. Results show an increase in γH2AX foci in a concentration-dependent manner upon treatment with Compound 1, indicating the presence of unrepaired DSBs within cells (FIG. 10A, B). The number of foci observed due to Compound 1 is comparable to those generated during siRNA knock down of Ligase IV. Cell cycle arrest and chromosomal aberrations are observed upon treatment of Compound 1 in HeLa cells (FIG. 9C-F). Thus, results indicate that Compound 1 interferes with NHEJ in the cells, resulting in the accumulation of unrepaired DSBs.

FIG. 9 depicts the effect of Compound 1 on chromosomal integrity and cell cycle progression. A. Immunofluorescence images of γH2AX foci formation in MCF7 cells following treatment with Compound 1 (50 and 100 μM). Cells are processed after about 24 h of treatment. In all panels, DMSO treated cells are used as control. Control and treated cells are fixed, permeabilized, blocked and incubated with anti-γH2AX primary antibody followed by incubation with appropriate biotinylated secondary antibody and strep-FITC. Propidium iodide is used as nuclear marker. Cells treated with secondary antibody alone served as negative control. Images are captured by Olympus DSU microscope. B. γH2AX foci formation in K562 cells following treatment with Compound 1 (50 and 100 μM). C, D. Cell cycle analysis upon Compound 1 treatment. HeLa cells (about 2×10⁵ cells/ml) are seeded and grown in serum free media for about 6 h. Following this, it is supplemented with serum containing media along with about 40 μM of Compound 1 and cells are harvested after 12, 18 and 24 h, stained with PI and analyzed by flow cytometry with WinMDI software. Bar diagram shows % cells present in the G2/M (C) and sub-G1 (D) phases of the cell cycle based on their DNA content. E. Effect of Compound 1 on induction of genomic instability. Giemsa stained metaphase spreads showing the chromosomal breaks generated upon Compound 1 (about 100 μM) treatment in HeLa cells. Chromosomal aberrations are indicated by arrows. DMSO treated cells are used as control. F. Table showing summary of chromosomal breaks analyzed following Compound 1 treatment. "ND" is none detected.

FIG. 10 depicts the evaluation of the effect of Compound 1 on NHEJ, accumulation of DSBs, and induction of cytotoxicity within the cells. A. Immunofluorescence showing γH2AX foci within MCF7 following treatment with Compound 1 (20, 40 and 100 μM, at about 24 h). DMSO treated cells are used as control. DAPI is nuclear marker. Images are captured by Zeiss Confocal laser scanning microscope. B. Detection of DSBs by γH2AX foci formation in MCF7 cells following treatment with siRNA against Ligase I, Ligase III and Ligase IV. Scrambled siRNA is used as the control. C, D. Bar diagram showing comparison of γH2AX foci in MCF7 (C) and HeLa (D) cells following treatment with different concentrations of Compound 1 and siRNA against different ligases. Data shown are from three independent experiments and in each case, foci from a minimum of about 50 cells are counted. Reduction in expression of ligases following siRNA transfection is confirmed by western blotting using anti Ligase I, Ligase III and Ligase IV. E. PI stained images for MCF7 cells treated with Compound 1 (for about 24 h) following alkaline single cell gel electrophoresis. The relative length and intensity of propidium iodide stained DNA tails to heads is proportional to the amount of DNA damage present in individual nuclei. Percentage of comets formed following alkaline single cell gel electrophoresis at indicated concentrations of Compound 1 in MCF7 and K562 cells. F. Comparison of cytotoxicity induced by Compound 1 on MCF7 and HeLa cells, as measured by MTT assay. DMSO treated cells serve as vehicle control. In panels A, D, E and G, significance levels are indicated (ns: not significant, *p<0.05, p<0.01, *p<0.001). The bar graph shows mean±SEM. G. Images of MCF7 cells treated with various concentrations of Compound 1 for about 5 days. H. Comparison of IC$_{50}$ of Compound 1 based on MTT assay in different cancer cell lines.

Example 10

Variation in the Effect of Ligase IV Inhibitor (Compound 1) Between Cancer Cells The cytotoxic effect of Compound 1 on various human cell lines derived from breast cancer (MCF7), cervical cancer (HeLa), lung cancer (A549), ovarian cancer (A2780), fibrosarcoma (HT1080), leukemia (K562 and CEM) and mouse breast cancer (EA), are compared using MTT assay. Results show a dose-dependent effect on cell proliferation of MCF7 and HeLa. A549, A2780 and HT1080 are also sensitive to Compound 1, with an IC$_{50}$ of about 35, 15 and 60 μM, respectively (FIG. 10H), while for leukemic cells it was >100 μM for CEM and K562.

Example 11

Role of Compound 1 in Preventing the Progression of Tumor in Mice Models and Resulting in Increased Life Span In order to assess the effect of Compound 1 on tumor progression, different mice models are tested. Results (FIG. 12) show that Compound 1 treatment (about 10 mg/kg, 6 doses) significantly reduces breast adenocarcinoma induced tumor, compared to that of untreated controls. The efficiency of Compound 1 on Dalton's lymphoma mouse model (about 20 mg/kg, 6 doses) is also tested. Neither tumor regression nor increase in lifespan is observed when treated with Compound 1 alone. FIG. 12 depicts the effect of Compound 1 on tumor progression in mice models bearing various tumors. A. Comparison of solid tumor progression generated by breast adenocarcinoma cells following treatment with Compound 1 for about 50 days. Six doses of Compound 1 (of about 10 mg/kg) are intramuscularly injected from $12^{th}$ day of EAC injection onwards, every alternate day. Data shown is from three independent batches of experiments containing 8 animals each. "Control" is mice injected with EAC cells, but not treated with Compound 1. "Compound 1" is the mice bearing tumor treated with Compound 1. Kaplan-Meier survival curves of Compound 1 treated EAC mice. B-1 and B-2. Kaplan-Meier survival curves of Compound 1 treated Dalton's lymphoma mice for about 30 days. Six doses of Compound 1 (of about 20 mg/kg) are administered every alternate day from $5^{th}$ day of DLA cells injection. Data shown is from two independent batches of experiments containing 10 animals each. "Control" is mice injected with DLA cells, "Compound 1" is the mice with DLA treated with Compound 1. C. Gross appearance of tumor and organs of mice following Compound 1 treatment after $25^{th}$ and $45^{th}$ days of tumor development. D. Histopathology of the tumor and liver of mice following Compound 1 treatment after $25^{th}$ and $45^{th}$ days of tumor development. In all panels, "Normal" is mice with no tumor, "Tumor" indicates mice induced with a tumor, "Treated" is tumor bearing mice after treatment with Compound 1.

Example 12

Significant Enhancement in the Sensitivity of Cancer to Radiation, Etoposide and Bleomycin when Employed Along with Compound 1

Above data indicates that the effect of Compound 1 is limited on tumor derived from DLA cells, and hence, combining Compound 1 along with existing treatment modalities that induce DNA strand breaks should enhance its sensitivity in this tumor model. To test this, mice bearing tumors are either irradiated (2 Gy, 2 doses) alone or in conjunction with Compound 1 (about 20 mg/kg) intraperitoneally. As expected a reduction in tumor growth is noted upon treatment with radiation alone, while in conjunction with Compound 1, it results in a significant decrease in tumor growth both on 7 and 14 days of treatment (FIG. 14A). Further, the effect of chemotherapeutic drugs like etoposide on Dalton's lymphoma with or without Compound 1 is tested. Compound 1 (20 mg/kg) is administered along etoposide (10 mg/kg) to mice bearing tumors intraperitoneally. A substantial reduction in tumor growth is seen, when both Compound 1 and etoposide are used together, as opposed to either alone. Similar result is observed when cancer cell lines are treated with bleomycin alone or in conjunction with Compound 1.

FIG. 14 depicts the evaluation of effect of Compound 1 on tumor progression in mice and proliferation of cancer cells following treatment with radiation and chemotherapeutic agents. A. Comparison of tumor progression induced by DLA cells following treatment with Compound 1 (about 20 mg/kg) for 14 days alone or in conjunction with gamma irradiation (2 Gy). Tumor animals are injected with six doses of Compound 1 and exposed to 2 doses of radiation from $5^{th}$ day of DLA injection onwards, every alternate day. Data shown is from two independent batches of experiments containing 5 animals each. "Control" is mice injected with DLA cells, "Compound 1" is the mice bearing tumor treated with Compound 1. "IR" is mice treated with gamma radiation, "IR +Compound 1" is mice exposed to gamma radiation and treated with Compound 1. B. Comparison of tumor progression generated by DLA cells following treatment with Compound 1 (about 20 mg/kg) and etoposide (about 10 mg/kg) for 14 days, either alone or together. "Control" is mice injected with DLA cells, "Compound 1" is the tumor mice treated with Compound 1. "Etoposide" is mice treated with etoposide, "Etoposide+Compound 1" is mice treated with etoposide and Compound 1. C. Comparison of tumor progression generated by DLA cells following treatment with Compound 1 (about 20 mg/kg) and 3-Aminobenzamide (about 10 mg/kg) for 14 days, alone or together. "Control" is mice injected with DLA cells, "Compound 1" is the tumor mice treated with Compound 1. "3-ABA" is mice treated with 3-Aminobenzamide, "3-ABA+Compound 1" is mice treated with 3-Aminobenzamide and Compound 1. D,E. Immunofluorescence showing γH2AX foci within the MCF7 (D) or HeLa (E) following treatment with bleomycin (of about 5 ng, for 3 h) alone or after treating with different concentrations of Compound 1 (20, 40 and 100 µM, 24 h). DMSO treated cells are used as vehicle control. γH2AX foci formation is detected as described in FIG. 10. Bar diagram showing comparison of γH2AX foci formation in MCF7 (D) or HeLa (E) cells following treatment with bleomycin and different concentrations of Compound 1. Data shown are from three independent experiments and in each case foci from a minimum of about 50 cells are counted. In panels A, B, C, D, E, significance levels are indicated (ns: not significant, *p<0.05, p<0.01, *p<0.001). The bar graph shows mean±SEM.

FIG. 13 depicts the effect of Compound 1 treatment on formation of DSBs with increase in time. A. HeLa cells are exposed to bleomycin (of about 10 ng) for about 3 h. Compound 1 (of about 40 µM) is added to the cells following removal of bleomycin, and allowed to repair for the indicated time. Images are captured using Carl Zeiss laser confocal microscope. B. The bar diagram representing mean number of DSBs/cell. A minimum of about 50 nuclei are counted in each sample. Bar graphs show mean±standard error mean (SEM) from two independent experiments.

Example 13

Assessment of Side Effects of Compound 1 Treatment on Mice

Six doses of Compound 1 are administrated to the BALB/c (n=7) mice for six alternative days. The results are shown in FIG. 11. No side-effects are observed on Compound 1 treatment.

FIG. 11 depicts the assessment of side effects of Compound 1 treatment on mice. A. Bar graph represents average weight changes in the both the controls (n=10) and Compound 1 treated mice (n=7). In all the cases, error bars indicate mean±standard error mean (SEM). B. Serum profile on mice administered with Compound 1 at day 28. Values indicated are mean±SEM (n=10).

Example 14

Activation of Intrinsic Pathway of Apoptosis and Induction of Cytotoxicity by Compound 1

Tumor regression in mice and increased cytotoxicity in cancer cell lines by Compound 1 is observed and therefore, the underlying mechanism of cell death is further studied.

Cell proliferation and downstream signaling are tested by immunohistochemical staining, in situ tunnel assay in tumor models and by western analysis of Compound 1 treated cancer cell lines. Results show an increase in phosphorylation of Ataxia telangiectasia mutated (ATM) upon treatment with Compound 1 (FIG. 15C). Activation of p53 and a concomitant decrease in MDM2 is also noted, which in turn results in activation of proapoptotic proteins, PUMA and BAX (FIG. 15C). Expressions of BCL2, the antiapoptotic protein, decreases while the levels of proapoptotic protein, BAD, remain unchanged (FIG. 15C). Besides, shorter fragment of MCL1, which acts as proapoptotic protein is upregulated in a dose-dependent manner (FIG. 15C). Overall, Compound 1 treatment destabilizes the balance between proapoptotic and antiapoptotic proteins leading to cell death. PARP1 plays a major role in DNA damage induced apoptosis and is the main target of caspases. A dose-dependent increase in PARP1 and Caspase 3 cleavage upon treatment with Compound 1 is observed (FIG. 15C). Activation of precursor Caspase 9 is also noted (FIG. 15C). Hence, above results indicate that accumulation of DSBs following Compound 1 treatment activates p53 mediated intrinsic pathway of apoptosis.

FIG. 15 depicts the analysis of mechanism of Compound 1 induced cytotoxicity in cancer cell lines and tumor models. A. Immunohistochemical studies for evaluation of cell proliferation, DNA repair and apoptotic markers following treatment of Compound 1 to mouse bearing EAC tumors. Antibodies against Ki67 (cell proliferation), ATM, pATM, p53BP1, p21 (DNA repair), BID and Caspase 3 (apoptosis) are used. Sections derived from mouse bearing 25 d old tumor (Compound 1 treated and untreated) are used for the study. B. Tunnel assay showing DNA fragmentation in the nuclei of Compound 1 treated tumor tissues. Green color indicates methyl green stained nuclei while brown indicates DNA breaks stained with diaminebenzidine, which is an indication of apoptosis. C. Western blotting for apoptotic and DNA repair markers in MCF7 cells following Compound 1 treatment. Extracts are prepared after about 24 h of Compound 1 (20 and 40 µM) treatment to the MCF7 cells and subjected to western blotting studies. GAPDH is used as loading control. D. Model depicting role of Compound 1 in the inhibition of NHEJ and activation of apoptotic pathway. Compound 1 interferes in binding of DNA Ligase IV/XRCC4 complex to the DNA breaks bound by KU70/KU80 heterodimeric complex. Hence, unrepaired DNA breaks accumulate in the cell, activating DNA damage response followed by induction of apoptosis by intrinsic pathway.

We claim:
1. A compound of formula I,

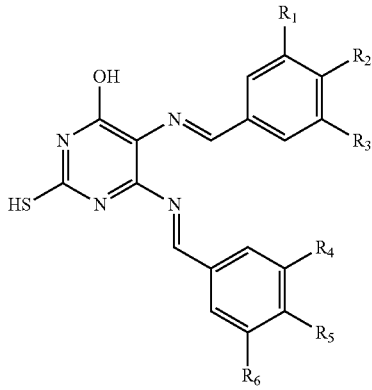

Formula I wherein, $R_1$, $R_2$, $R_3$, $R_4$, $R_5$, and $R_6$ are hydrogen; or
$R_1$, $R_3$, $R_4$ and $R_6$ are hydrogen, and $R_2$ and $R_5$ are chlorine; or
$R_1$, $R_3$, $R_4$ and $R_6$ are hydrogen, and $R_2$ and $R_5$ are methyl; or
$R_1$, $R_3$, $R_4$ and $R_6$ are hydrogen, and $R_2$ and $R_5$ are nitro; or
$R_1$, $R_3$, $R_4$ and $R_6$ are hydrogen, and $R_2$ and $R_5$ are methoxy; or
$R_1$, $R_2$, $R_3$, $R_4$, $R_5$ and $R_6$ are methoxy;
its tautomers or salts thereof.

2. The compound as claimed in claim 1, which is in the form of its salt, wherein the salt is a sodium salt or a potassium salt or a combination thereof.

3. A method for preparing a compound of formula I,

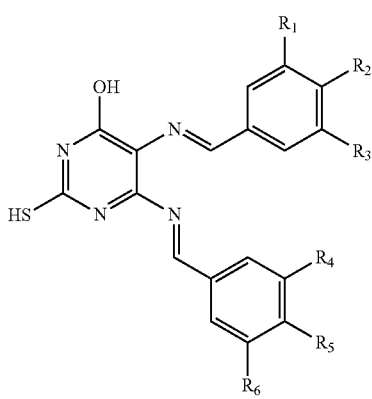

Formula I wherein, $R_1$, $R_2$, $R_3$, $R_4$, $R_5$, and $R_6$ are hydrogen; or
$R_1$, $R_3$, $R_4$ and $R_6$ are hydrogen, and $R_2$ and $R_5$ are chlorine; or
$R_1$, $R_3$, $R_4$ and $R_6$ are hydrogen, and $R_2$ and $R_5$ are methyl; or
$R_1$, $R_3$, $R_4$ and $R_6$ are hydrogen, and $R_2$ and $R_5$ are nitro; or
$R_1$, $R_3$, $R_4$ and $R_6$ are hydrogen, and $R_2$ and $R_5$ are methoxy; or
$R_1$, $R_2$, $R_3$, $R_4$, $R_5$ and $R_6$ are methoxy;
its tautomers or salts thereof;
comprising steps of:
a) reacting 5,6-diamino-4-hydroxy-2-mercaptopyrimidine with substituted or unsubstituted benzaldehyde to obtain a corresponding compound with monoimine functionality; and
b) reacting the compound of monoimine functionality of step (a) with substituted or unsubstituted benzaldehyde to obtain the compound of formula I,
wherein the substituted or unsubstituted benzaldehyde are the same in both steps (a) and (b).

4. The method as claimed in claim 3, wherein the monoimine functionality in the compound obtained in step (a) is

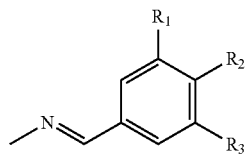

wherein, $R_1$, $R_2$ and $R_3$ are hydrogen; or
$R_1$ and $R_3$ are hydrogen and $R_2$ is chlorine; or
$R_1$ and $R_3$ are hydrogen and $R_2$ is methyl; or
$R_1$ and $R_3$ are hydrogen and $R_2$ is nitro; or
$R_1$ and $R_3$ are hydrogen and $R_2$ is methoxy; or
$R_1$, $R_2$ and $R_3$ are methoxy.

5. The method as claimed in claim 3, in which the compound of formula I is in the form of its salt, wherein the salt is a sodium salt or a potassium salt or a combination thereof.

6. The method as claimed in claim 3, wherein the substituted benzaldehyde is selected from the group consisting of 4-chlorobenzaldehyde, 4-tolualdehyde, 4-nitrobenzaldehyde, 4-anisaldehyde, and 3,4,5-trimethoxybenzaldehyde.

7. The method as claimed in claim 3, wherein the reacting is carried out in dimethyl formamide (DMF) solvent in the presence of an acid.

8. The method as claimed in claim 7, wherein the acid is acetic acid.

9. The method as claimed in claim 3, wherein the steps (a) and (b) further comprise optional steps of isolation, re-crystallization and purification.

10. A method of arresting DNA double-strand break (DSB) repair selected from the group consisting of breast cancer, cervical cancer, ovarian cancer, fibrous sarcoma, lung cancer and leukemia, said method comprising contacting (5E,6E)-5,6-bis(benzylideneamino)-2-mercaptopyrimidin-4-ol (Compound 1), or its tautomers or salts thereof, with DNA Ligase for arresting the DNA double-strand break (DSB) repair Compound 1

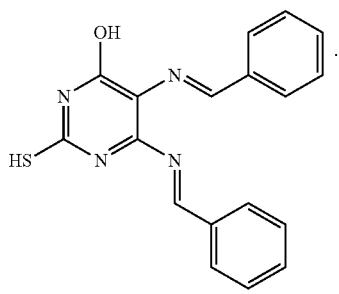

11. The method as claimed in claim 10, wherein the DNA Ligase is DNA Ligase IV.

12. The method as claimed in claim 10, wherein the DNA double-strand break (DSB) repair is carried out by non-homologous end joining (NHEJ) pathway.

13. The method as claimed in claim 12, wherein the non-homologous end joining (NHEJ) pathway comprises enzyme DNA Ligase IV.

14. The method as claimed in claim 10, wherein the Compound 1 inhibits the activity of DNA Ligase IV.

15. The method as claimed in claim 14, wherein the inhibition is carried out by binding of the compound to DNA binding domain of the DNA Ligase IV.

16. The method as claimed in claim 15, wherein the binding results in the arrest of DNA double-strand break (DSB) repair.

17. A method of treating cancer selected from the group consisting of breast cancer, cervical cancer, ovarian cancer, fibrous sarcoma, lung cancer and leukemia, comprising administering to a subject in need of such treatment an effective amount of (5E,6E)-5,6-bis(benzylideneamino)-2-mercaptopyrimidin-4-ol (Compound 1), or its tautomers or salts thereof Compound 1

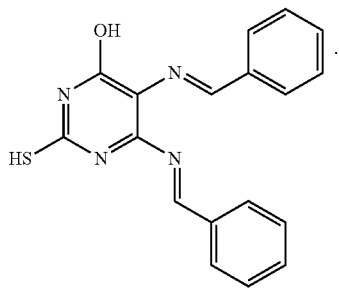

18. The compound as claimed in claim 2, which is the form of its salt, wherein the salt is

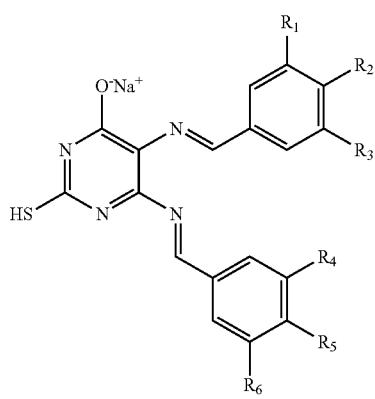

or

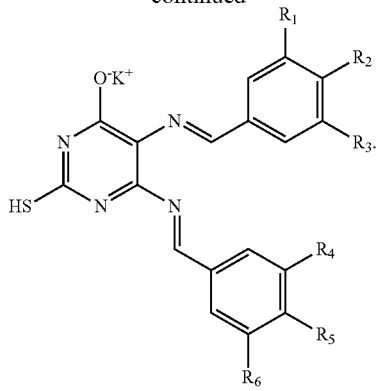

19. The method as claimed in claim 5, in which the compound of formula I is in the form of its salt, wherein the salt is

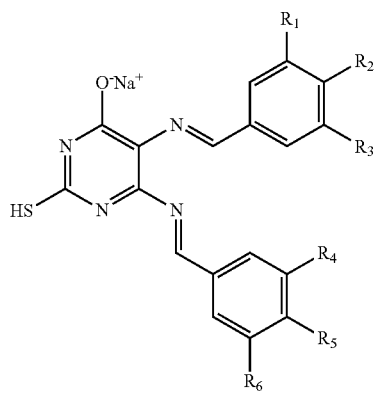

or

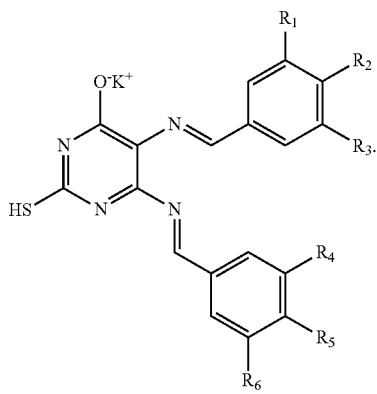

20. The method as claimed in claim 5, wherein the salt is prepared by reacting the compound of formula (I) obtained in step (b) with hydroxide of sodium or potassium.

* * * * *

SEQUENCE LISTING

```
<160> NUMBER OF SEQ ID NOS: 16

<210> SEQ ID NO 1
<211> LENGTH: 74
<212> TYPE: DNA
<213> ORGANISM: Artificial Sequence
<220> FEATURE:
<223> OTHER INFORMATION: Oligomer - TSK1
<220> FEATURE:
<221> NAME/KEY: primer_bind
<222> LOCATION: (1)..(74)

<400> SEQUENCE: 1
atccctctag atatcgggcc ctcgatccgg tactactcga gccggctagc ttcgatgctg      60
cagtctagcc tgag                                                        74

<210> SEQ ID NO 2
<211> LENGTH: 74
<212> TYPE: DNA
<213> ORGANISM: Artificial Sequence
<220> FEATURE:
<223> OTHER INFORMATION: Oligomer - TSK2
<220> FEATURE:
<221> NAME/KEY: primer_bind
<222> LOCATION: (1)..(74)

<400> SEQUENCE: 2
atcctcaggc tagactgcag catcgaagct agccggctcg agtagtaccg gatcgagggc      60
ccgatatcta gagg                                                        74

<210> SEQ ID NO 3
<211> LENGTH: 75
<212> TYPE: DNA
<213> ORGANISM: Artificial Sequence
<220> FEATURE:
<223> OTHER INFORMATION: Oligomer - VK7
<220> FEATURE:
<221> NAME/KEY: primer_bind
<222> LOCATION: (1)..(75)
```

-continued

```
<400> SEQUENCE: 3
gggctctaga tatcgggccc tcgatccggt actactcgag ccggctagct tcgatgctgc    60
agtctagcct ggccc                                                    75

<210> SEQ ID NO 4
<211> LENGTH: 75
<212> TYPE: DNA
<213> ORGANISM: Artificial Sequence
<220> FEATURE:
<223> OTHER INFORMATION: Oligomer - VK8
<220> FEATURE:
<221> NAME/KEY: primer_bind
<222> LOCATION: (1)..(75)

<400> SEQUENCE: 4
gggccaggct agactgcagc atcgaagcta gccggctcga gtagtaccgg atcgagggcc    60
cgatatctag agccc                                                    75

<210> SEQ ID NO 5
<211> LENGTH: 75
<212> TYPE: DNA
<213> ORGANISM: Artificial Sequence
<220> FEATURE:
<223> OTHER INFORMATION: Oligomer - VK11
<220> FEATURE:
<221> NAME/KEY: primer_bind
<222> LOCATION: (1)..(75)

<400> SEQUENCE: 5
aattctcagg ctagactgca gcatcgaagc tagccggctc gagtagtacc ggatcgaggg    60
cccgatatct agagg                                                    75

<210> SEQ ID NO 6
<211> LENGTH: 67
<212> TYPE: DNA
<213> ORGANISM: Artificial Sequence
<220> FEATURE:
<223> OTHER INFORMATION: Oligomer - VK13
<220> FEATURE:
<221> NAME/KEY: primer_bind
<222> LOCATION: (1)..(67)

<400> SEQUENCE: 6
ggctagactg cagcatcgaa gctagccggc tcgagtagta ccggatcgag ggcccgatat    60
ctagagg                                                             67

<210> SEQ ID NO 7
<211> LENGTH: 24
<212> TYPE: DNA
<213> ORGANISM: Artificial Sequence
<220> FEATURE:
<223> OTHER INFORMATION: Oligomer - MS42
<220> FEATURE:
<221> NAME/KEY: primer_bind
<222> LOCATION: (1)..(24)

<400> SEQUENCE: 7
tggatccatg gctgcctcac aaac                                          24
```

```
<210> SEQ ID NO 8
<211> LENGTH: 25
<212> TYPE: DNA
<213> ORGANISM: Artificial Sequence
<220> FEATURE:
<223> OTHER INFORMATION: Oligomer - MS43
<220> FEATURE:
<221> NAME/KEY: primer_bind
<222> LOCATION: (1)..(25)

<400> SEQUENCE: 8
cctcgagctc actaggaaac ctagc                                          25

<210> SEQ ID NO 9
<211> LENGTH: 23
<212> TYPE: DNA
<213> ORGANISM: Artificial Sequence
<220> FEATURE:
<223> OTHER INFORMATION: Oligomer - MS48
<220> FEATURE:
<221> NAME/KEY: primer_bind
<222> LOCATION: (1)..(23)

<400> SEQUENCE: 9
attcggatcc atggtgcggt cgg                                            23

<210> SEQ ID NO 10
<211> LENGTH: 25
<212> TYPE: DNA
<213> ORGANISM: Artificial Sequence
<220> FEATURE:
<223> OTHER INFORMATION: Oligomer - MS49
<220> FEATURE:
<221> NAME/KEY: primer_bind
<222> LOCATION: (1)..(25)

<400> SEQUENCE: 10
ctatgcggcc gcctatatca tgtcc                                          25

<210> SEQ ID NO 11
<211> LENGTH: 23
<212> TYPE: DNA
<213> ORGANISM: Artificial Sequence
<220> FEATURE:
<223> OTHER INFORMATION: Oligomer - MS52
<220> FEATURE:
<221> NAME/KEY: primer_bind
<222> LOCATION: (1)..(23)

<400> SEQUENCE: 11
gaattcatgt cagggtggga gtc                                            23

<210> SEQ ID NO 12
<211> LENGTH: 30
<212> TYPE: DNA
<213> ORGANISM: Artificial Sequence
<220> FEATURE:
<223> OTHER INFORMATION: Oligomer - MS53
<220> FEATURE:
<221> NAME/KEY: primer_bind
<222> LOCATION: (1)..(30)

<400> SEQUENCE: 12
catatgatat ctccttctta tcagtcctgg                                     30

<210> SEQ ID NO 13
<211> LENGTH: 21
<212> TYPE: DNA
```

```
<213> ORGANISM: Artificial Sequence
<220> FEATURE:
<223> OTHER INFORMATION: Oligomer - MS61
<220> FEATURE:
<221> NAME/KEY: primer_bind
<222> LOCATION: (1)..(21)

<400> SEQUENCE: 13
ttactcgaga gctagcattg g                                              21

<210> SEQ ID NO 14
<211> LENGTH: 18
<212> TYPE: DNA
<213> ORGANISM: Artificial Sequence
<220> FEATURE:
<223> OTHER INFORMATION: Oligomer - MS68
<220> FEATURE:
<221> NAME/KEY: primer_bind
<222> LOCATION: (1)..(18)

<400> SEQUENCE: 14
atccgttgaa gcctgctt                                                  18

<210> SEQ ID NO 15
<211> LENGTH: 25
<212> TYPE: DNA
<213> ORGANISM: Artificial Sequence
<220> FEATURE:
<223> OTHER INFORMATION: Oligomer - MS69
<220> FEATURE:
<221> NAME/KEY: primer_bind
<222> LOCATION: (1)..(25)

<400> SEQUENCE: 15
tgacatacta acttgagcga aacgg                                          25

<210> SEQ ID NO 16
<211> LENGTH: 43
<212> TYPE: DNA
<213> ORGANISM: Artificial Sequence
<220> FEATURE:
<223> OTHER INFORMATION: Oligomer - MS70
<220> FEATURE:
<221> NAME/KEY: primer_bind
<222> LOCATION: (1)..(43)

<400> SEQUENCE: 16
ccgtttcgct caagttagta tgtcaaagca ggcttcaacg gat                      43
```